(12) United States Patent
Walter et al.

(10) Patent No.: US 11,369,437 B2
(45) Date of Patent: Jun. 28, 2022

(54) ALIGNMENT APPARATUS FOR USE IN SURGERY

(71) Applicant: Navbit Holdings Pty Limited, North Sydney (AU)

(72) Inventors: William L. Walter, North Sydney (AU); Daniel Marsden-Jones, North Sydney (AU)

(73) Assignee: VIVID SURGICAL PTY LTD

( * ) Notice: Subject to any disclaimer, the term of this patent is extended or adjusted under 35 U.S.C. 154(b) by 175 days.

(21) Appl. No.: 16/349,609

(22) PCT Filed: Nov. 14, 2017

(86) PCT No.: PCT/AU2017/051251
§ 371 (c)(1),
(2) Date: May 13, 2019

(87) PCT Pub. No.: WO2018/085900
PCT Pub. Date: May 17, 2018

(65) Prior Publication Data
US 2020/0268454 A1   Aug. 27, 2020

(30) Foreign Application Priority Data
Nov. 14, 2016   (AU) ............................... 2016904640

(51) Int. Cl.
*A61B 34/20*   (2016.01)
*A61B 17/16*   (2006.01)
(Continued)

(52) U.S. Cl.
CPC .......... *A61B 34/20* (2016.02); *A61B 17/1671* (2013.01); *A61B 17/1675* (2013.01);
(Continued)

(58) Field of Classification Search
CPC ..................................................... A61F 2/4609
See application file for complete search history.

(56) References Cited

U.S. PATENT DOCUMENTS 7,484,305 B2    2/2009   Sherry et al.
9,931,059 B2 *  4/2018   Borja ................... A61B 5/1079
(Continued)

FOREIGN PATENT DOCUMENTS

AU    2009273863 B2    1/2010
AU    2009295253 B2    3/2010
(Continued)

OTHER PUBLICATIONS

Extended European Search Report for application No. EP 17869979.91 dated Feb. 19, 2020. 7 pages.
(Continued)

*Primary Examiner* — Andrew Yang

(57) ABSTRACT

An apparatus comprising: a medical tool moveable to a desired orientation relative to a bone region for implantation of a medical implant; and an electronic orientation sensor transitionable between a first location fixed relative to the bone region of the patient and a second location on the medical tool; wherein, at the first location, the orientation sensor is adapted to record a reference orientation of the bone region of the patient, and, at the second location, the orientation sensor is adapted to determine an orientation of the medical tool relative to the reference orientation, wherein recording the reference orientation comprises measuring a gravity vector relative to the orientation sensor.

11 Claims, 21 Drawing Sheets

(51) Int. Cl.
*A61B 17/17* (2006.01)
*A61F 2/46* (2006.01)

(52) U.S. Cl.
CPC ...... *A61B 17/1714* (2013.01); *A61B 17/1764* (2013.01); *A61F 2/461* (2013.01); *A61F 2/4609* (2013.01); A61B 2034/2048 (2016.02); A61F 2002/4687 (2013.01)

(56) References Cited

U.S. PATENT DOCUMENTS

| | | |
|---|---|---|
| 10,206,714 B2 | 2/2019 | van der Walt et al. |
| 10,271,963 B2 | 4/2019 | Lye |
| 10,603,115 B2 | 3/2020 | van der Walt et al. |
| 2011/0098712 A1 | 4/2011 | Sherry et al. |
| 2011/0160572 A1 | 6/2011 | McIntosh et al. |
| 2012/0157887 A1 | 6/2012 | Fanson et al. |
| 2012/0172884 A1 | 7/2012 | Zheng et al. |
| 2012/0203140 A1 | 8/2012 | Malchau et al. |
| 2012/0209117 A1 | 8/2012 | Mozes et al. |
| 2012/0209394 A1 | 8/2012 | Bojarski et al. |
| 2012/0245647 A1 | 9/2012 | Kunz et al. |
| 2013/0053859 A1 | 2/2013 | Penenberg |
| 2014/0276871 A1 | 9/2014 | Sherman et al. |
| 2015/0150585 A1 | 6/2015 | Penenberg |
| 2015/0272478 A1 | 10/2015 | Borja |
| 2016/0220318 A1 | 8/2016 | Falardeau et al. |
| 2016/0249968 A1 | 9/2016 | Walter et al. |
| 2021/0093401 A1 | 4/2021 | Falardeau et al. |

FOREIGN PATENT DOCUMENTS

| | | |
|---|---|---|
| AU | 2011341678 B2 | 6/2012 |
| AU | 2013303055 B2 | 2/2014 |
| AU | 2015201383 A1 | 4/2015 |
| AU | 2016219992 B2 | 8/2016 |
| AU | 2018208638 A1 | 8/2018 |
| WO | 2012084739 A1 | 6/2012 |
| WO | 2012109361 A3 | 8/2012 |
| WO | 2014000053 A1 | 1/2014 |
| WO | 2014028227 A1 | 2/2014 |
| WO | 2015054745 A1 | 4/2015 |
| WO | 2018169980 A1 | 9/2018 |
| WO | 2018169995 A1 | 9/2018 |

OTHER PUBLICATIONS

International-type search for provisional patent application for application No. 2016904640 dated May 16, 2017, 12 pages.

\* cited by examiner

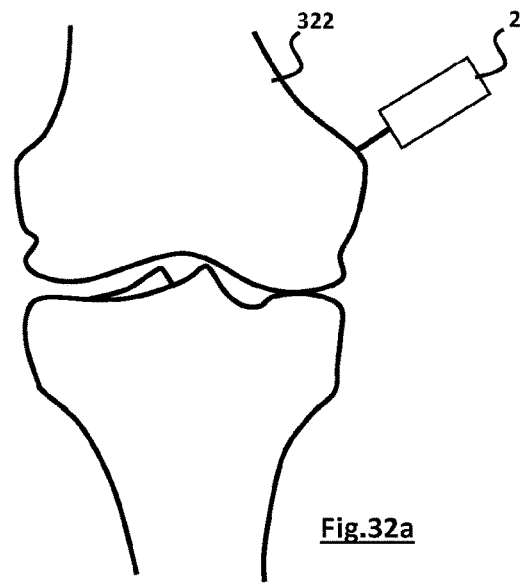
Fig.32a
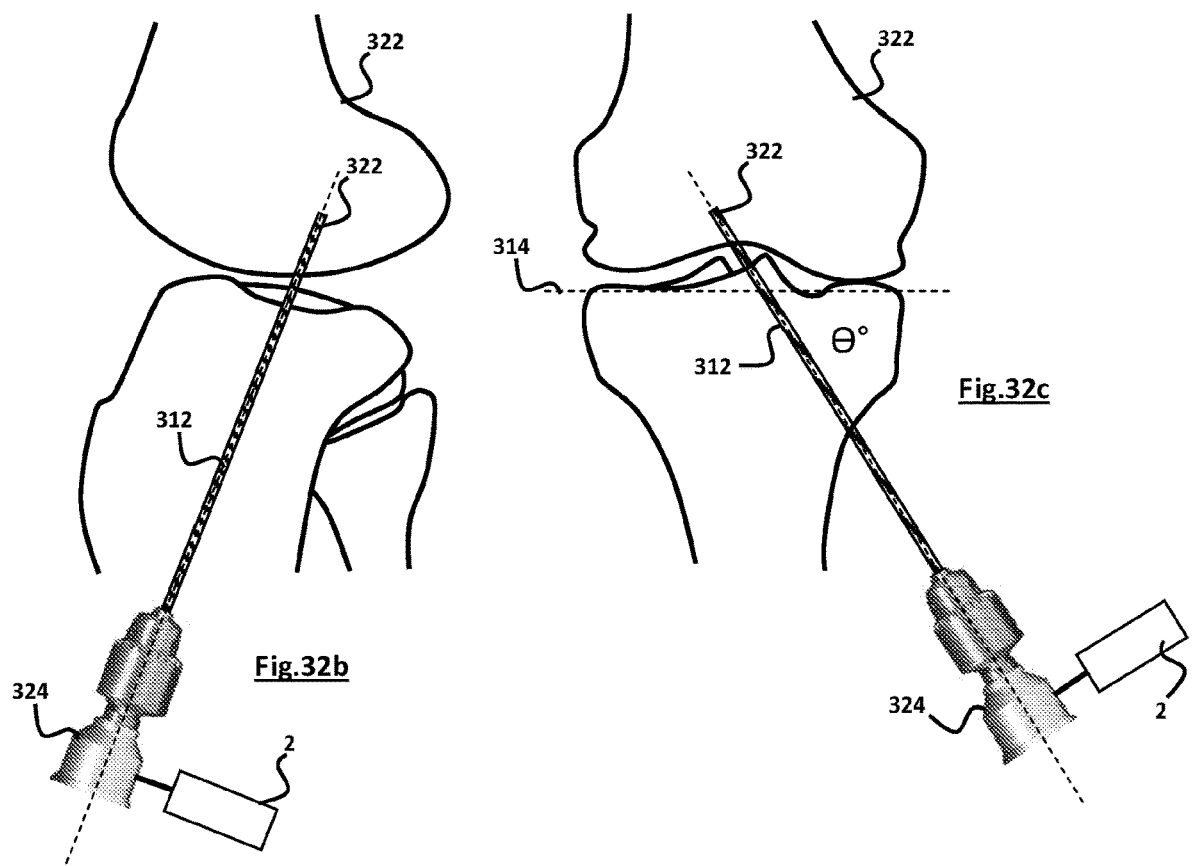
Fig.32b
Fig.32c

ALIGNMENT APPARATUS FOR USE IN SURGERY

TECHNICAL FIELD

The present disclosure relates to alignment apparatus for use in surgery.

BACKGROUND

In surgical procedures involving medical implants, the orientation of an implant relative to a patient's body can be critical to the success of such procedures.

For example, hip arthroplasty involves the replacement of the hip joint by a prosthetic implant. The prosthetic implant can consist of different parts, including an acetabular cup designed to locate in the acetabulum (hip socket). The acetabular cup is located in position using an acetabular cup impactor, which generally takes the form of an elongate rod, having the cup at one end, and which is used to insert and orient the cup in the acetabulum. To ensure that an acetabular cup functions correctly, and does not wear significantly or cause damage to a patient, it is important that the cup is oriented and positioned correctly in the acetabulum.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Various aspects of the present disclosure provide apparatus, and methods, for use in surgical procedures in which accurate orientation of an implant relative to a patient's body is critical to the success of such procedures. Some aspects relate to procedures where an acetabular cup impactor is used to implant an acetabular cup at the acetabulum of a patient's pelvic region. A device can be mounted on the acetabular cup impactor and/or the patient's pelvic region and adapted to sense relative angular displacement of the impactor and pelvic region in order to assist with guidance of the acetabular cup impactor to a desired orientation. Other aspects relate to procedures where a pedicle screw is driven into a patient's vertebra, the inclination and anteversion of the screw being critical to such procedures.

According to one aspect, the present disclosure provides an apparatus comprising:

a medical tool moveable to a desired orientation relative to a bone region for implantation of a medical implant; and an electronic orientation sensor transitionable between a first location fixed relative to the bone region of the patient and a second location on the medical tool;

wherein, at the first location, the orientation sensor is adapted to record a reference orientation of the bone region of the patient, and, at the second location, the orientation sensor is adapted to determine an orientation of the medical tool relative to the reference orientation, wherein recording the reference orientation comprises:

measuring a gravity vector relative to the orientation sensor.

According to another aspect, the present disclosure provides method of positioning an acetabular cup impactor, comprising:

locating an electronic orientation sensor at a first location fixed relative to a bone region of a patient, using the electronic orientation sensor located at the first location to record a reference orientation of the patient's bone region by:

measuring a gravity vector relative to the orientation sensor;

transitioning the electronic orientation sensor from the first location to a second location on a medical tool, the medical tool being moveable to a desired orientation relative to the patient's bone region for implantation of a medical implant, and using the orientation sensor located at the second location to determine an orientation of the medical tool relative to the reference orientation.

According to yet another aspect, the present disclosure provides an electronic orientation sensor, the sensor being transitionable from a first location on a patient's pelvic region to a second location on an acetabular cup impactor, the acetabular cup impactor moveable to a desired orientation relative to a patient's pelvic region for implantation of an acetabular cup, wherein, at the first location, the orientation sensor is adapted to record a reference orientation of the patient's pelvic region, and at the second location the orientation sensor is adapted to determine an orientation of the acetabular cup impactor relative to the reference orientation.

According to another aspect, the present disclosure provides a method of determining an orientation of an acetabular cup impactor, comprising:

recording a reference orientation of a bone region of a patient using an electronic orientation sensor located at a first location fixed relative to the bone region by:

measuring a gravity vector relative to the orientation sensor; and determining an orientation of a medical tool relative to the reference orientation using the electronic orientation sensor when the electronic orientation sensor is located at a second location on the medical tool after being transitioned to the second location from the first location, the medical tool being moveable to a desired orientation relative to the bone region for implantation of a medical implant.

According to yet another aspect, the present disclosure provides software that, when installed on a computing device, causes the computing device to perform the method of the immediately preceding aspect.

According to another aspect, the present disclosure provides a method of determining a reference orientation of an orientation sensor connected to a human body, the reference orientation relative to the human body, the method comprising:

aligning the orientation sensor with a transverse vector intersecting two bilaterally symmetric points on the body;

measuring, by the orientation sensor, a gravity vector with the body in a supine or prone position; and determining a longitudinal vector of the body relative to the orientation sensor based on the measured gravity vector and the transverse vector.

According to yet another aspect, the present disclosure provides a method of determining a reference orientation of an orientation sensor connected to a human body, the reference orientation relative to the human body, the method comprising:

measuring, by the orientation sensor, a gravity vector with the body in a supine or prone position;

determining a longitudinal vector of the body relative to the orientation sensor by measuring, using the sensor, the orientation of the sensor while rotating the body about its longitudinal axis; and determining a transverse vector of the body relative to the sensor based on the determined anteroposterior and longitudinal vectors.

According to another aspect, the present disclosure provides a method of determining a reference orientation of an orientation sensor connected to a human body, the reference orientation relative to the human body, the method comprising:

measuring, by the orientation sensor, a gravity vector with the body in a supine or prone position;

measuring, by the orientation sensor, the gravity vector with the body in a lateral position;

determining a transverse vector of the body relative to the sensor based on the gravity vector measured in the lateral position; and determining a longitudinal vector of the body relative to the sensor based on the determined gravity and transverse vectors.

According to another aspect, the present disclosure provides a method of determining a reference orientation of an orientation sensor connected to a human body, the reference orientation relative to the human body, the method comprising:

receiving alignment data indicative of the orientation of the orientation sensor relative to a transverse vector intersecting two bilaterally symmetric points on the body and a gravity vector with the body in a supine or prone position;

determining an anteroposterior vector of the body relative to the orientation sensor based on the measured gravity vector; and determining a longitudinal vector of the body relative to the orientation sensor based on the measured gravity vector and the transverse vector.

According to another aspect, the present disclosure provides a method of determining a reference orientation of an orientation sensor connected to a human body, the reference orientation relative to the human body, the method comprising:

receiving alignment data indicative of the orientation of the orientation sensor relative to a gravity vector with the body in a supine or prone position and a longitudinal vector of the body relative to the sensor;

determining an anteroposterior vector of the body relative to the sensor based on the measured gravity vector; and determining a transverse vector of the body relative to the sensor based on the determined anteroposterior and longitudinal vectors.

According to another aspect, the present disclosure provides a method of determining a reference orientation of an orientation sensor connected to a human body, the reference orientation relative to the human body, the method comprising:

receiving alignment data indicative of the orientation of the orientation sensor relative to a gravity vector with the body in a supine or prone position and the gravity vector with the body in a lateral position;

determining an anteroposterior vector of the body relative to the sensor based on the measured gravity vector;

determining a transverse vector of the body relative to the sensor based on the gravity vector measured in the lateral position; and determining a longitudinal vector of the body relative to the sensor based on the determined anteroposterior and transverse vectors.

According to another aspect, the present disclosure provides hip arthroplasty apparatus comprising:

an acetabular cup impactor moveable to a desired orientation relative to a patient's pelvic region for implantation of an acetabular cup; and an electronic orientation sensor transitionable between a first location on the patient's pelvic region and a second location on the acetabular cup impactor;

a mating component configured to mate with a portion of the patient's pelvis in a predetermined orientation;

wherein, at the first location, the orientation sensor is coupled to or integrated with the mating component and is adapted to record a reference orientation of the patient's pelvic region, and, at the second location, the orientation sensor is adapted to determine an orientation of the acetabular cup impactor relative to the reference orientation.

According to another aspect, the present disclosure provides a method of positioning an acetabular cup impactor, comprising:

locating mating component at a first location on a patient's pelvic region, the mating component configured to mate with a portion of the patient's pelvic region at the first location, the mating component having coupled thereto an electronic orientation sensor, using the electronic orientation sensor located at the first location to record a reference orientation of the patient's pelvic region, transitioning the electronic orientation sensor from the first location to a second location on an acetabular cup impactor, the acetabular cup impactor being moveable to a desired orientation relative to the patient's pelvic region for implantation of an acetabular cup, and using the orientation sensor located at the second location to determine an orientation of the acetabular cup impactor relative to the reference orientation.

In one embodiment, the orientation sensor is mounted or adapted to be mounted on the acetabular cup impactor, e.g. at a distal end of a handle of the impactor, via releasable fixation means. The apparatus may comprise a mount that is configured to engage both the orientation sensor and the impactor and releasably fix the positions of the orientation sensor and the impactor relative to each other. The mount may include two clamp portions, for example, adapted to clamp to the orientation sensor and the impactor, respectively. Similarly, the orientation sensor may be mounted or adapted to be mounted on the pelvic region via releasable fixation means. The apparatus may comprise a mount that is configured to engage both the orientation sensor and the pelvic region and releasably fix the positions of the orientation sensor and the pelvic region relative to each other. The mount may include two clamp portions, for example, adapted to clamp to the orientation sensor and the pelvic region, respectively. Generally, when located at the first or second location, on the pelvic region and impactor, respectively, the orientation sensor may or may not directly contact the pelvic region or impactor. However, the orientation of the orientation sensor may be substantially fixed relative to the pelvic region or impactor.

The orientation sensor may be adapted to determine the orientation of the acetabular cup impactor relative to the reference orientation in three-dimensional space. The relative orientation of the longitudinal axis of the handle and shaft of the acetabular cup impactor may be determined. Relative orientation may be determined as a degree of relative rotation about three orthogonal axes of a coordinate system (e.g. as Euler angles or otherwise). The reference orientation may provide for a local coordinate system.

The orientation sensor may determine changes in orientation based on gravitational fields, magnetic fields, and/or acceleration, for example. The orientation sensor may calculate the orientation of the impactor with respect to the specified reference orientation through monitoring of degrees of rotation about multiple axes as it transitions from the first location on the pelvic region to the second location on the impactor and as it moves during any subsequent movement of the impactor. The orientation sensor may comprise one or more of a gyroscope, a magnetic field sensor, an accelerometer, angular position sensor, and/or rotary sensor and/or one or more other types of movement or absolute or relative position sensors.

The apparatus and/or orientation sensor may comprise an output device adapted to provide information about the relative orientation of the impactor and/or the reference orientation to a clinician or other user, e.g. via text, graphics, audio and/or tactile feedback. The output device may comprise a display, speaker and/or vibrator, for example.

The apparatus and/or orientation sensor may comprise a processor adapted to determine the reference orientation and/or the relative orientation of the impactor relative to the reference orientation.

The apparatus and/or orientation sensor may comprise an input device adapted to receive an input from the clinician or other user. The input device may include one or more buttons, a keyboard, a touch sensitive screen, voice detector or otherwise. The input device may receive input from the user about a desired orientation of the impactor, e.g. desired anteversion and/or inclination angles, and/or measured orientation data, e.g. measured anteversion and/or inclination angles. The input device may receive input from the user indicative of when the orientation sensor is located on the pelvic region. The providing of an input that is indicative of when the orientation sensor is located on the pelvic region may trigger recording of the reference orientation by the orientation sensor.

The desired orientation of the impactor may correspond to an optimum implantation orientation of the acetabular cup. The optimum orientation can be defined by angles of inclination (abduction) and/or anteversion, for example. The desired orientation may be a desired angle of anteversion or a desired angle of inclination or a desired combination of anteversion and inclination angles. Anteversion and inclination angles can be defined differently, depending on whether anatomic, radiographic or operative reference frames are used. In discussions herein, desired and measured anteversion and inclination angles are defined in respect of the anatomic reference frame unless indicated otherwise. Nevertheless, the techniques described are not limited to using angles defined with respect to this reference frame only.

The desired orientation of the impactor may depend on surgical circumstances including the anatomy of the patient and preferences of the surgeon. A commonly desired anteversion angle is about 20° and a commonly desired inclination angle is about 45°. Nevertheless, the desired anteversion may be anywhere between −35° and 60°, or 0° and 40°, for example, and the desired inclination may be anywhere between 25° and 60°, or 35° and 50, for example.

In one embodiment, any one or more of the orientation sensor, the processor, the input device and the output device may be comprised in a single electronic device, such as a smartphone, tablet computer, or similar. The electronic device may run a software program or software "app" adapted to control one or more of these elements.

While an electronic orientation sensor can be used to determine orientation of an acetabular cup impactor as discussed above, an electronic orientation sensor may also be used to monitor changes in orientation in the pelvic region during surgery.

In particular, according to one aspect, the present disclosure provides hip arthroplasty apparatus comprising an electronic orientation sensor locatable on a patient's pelvic region, wherein the orientation sensor is adapted to record a reference orientation of the patient's pelvic region and subsequently monitor changes in orientation of the pelvic region relative to the reference orientation.

According to another aspect, the present disclosure provides a method of monitoring changes in orientation of a pelvic region during surgery, comprising:

locating an electronic orientation sensor on a patient's pelvic region and using the electronic orientation sensor to record a reference orientation of the patient's pelvic region, using the orientation sensor to monitor changes in orientation of the pelvic region relative to the reference orientation.

According to yet another aspect, the present disclosure provides an electronic orientation sensor, the sensor being locatable on a patient's pelvic region where it is adapted to record a reference orientation of the patient's pelvic region and monitor changes in orientation of the pelvic region relative to the reference orientation.

According to another aspect, the present disclosure provides a method of monitoring changes in orientation of a pelvic region during surgery, comprising:

recording a reference orientation of a patient's pelvic region using an electronic orientation sensor located on the patient's pelvic region, and monitoring changes in the orientation of the pelvic region relative to the reference orientation.

According to yet another aspect, the present disclosure provides software that when, installed on a computing device, causes the computing device to perform the method of the immediately preceding aspect.

The orientation sensor may be configured as described above with respect to earlier aspects. The apparatus and/or orientation sensor may comprise an output device and/or an input device as described above with respect to earlier aspects.

Monitoring of changes in the orientation of the pelvic region may be used independently of or in conjunction with determining the orientation of the acetabular cup impactor as described with respect to earlier aspects.

In general, a pelvic region can move during surgery and this can impart error into the procedure in which the orientation of the acetabular cup impactor is determined relative to a reference orientation of the pelvic region. In effect, movement of the pelvic region can cause the recorded reference orientation to be inaccurate. By monitoring changes in the orientation of the pelvic region, correction can be applied. In one embodiment, an orientation sensor is located on the pelvic region and another orientation sensor, after having recorded the reference orientation of the pelvic region, is located on the acetabular cup impactor. The orientation sensor located on the pelvic region is adapted to communicate, e.g., wirelessly or otherwise, with the orientation sensor located on the acetabular cup impactor to provide information about changes in the orientation of the pelvic region, allowing correction of a recorded reference orientation to be made. Correction may be made substantially in 'real-time'.

Various other aspects of the present disclosure also provide apparatus, and methods, for use in hip arthroplasty, in which an acetabular cup impactor is used to implant an acetabular cup at the acetabulum of a patient's pelvic region. An image capture device can be mounted on one of the acetabular cup impactor and the patient's pelvic region and adapted to capture images of the other of the acetabular cup impactor and pelvic region. The images can be presented on a display and can include one or more indicia, e.g., markers. Through observation of the one or more indicia in the images, the acetabular cup impactor can be guided to a desired orientation.

According to one aspect, the present disclosure provides hip arthroplasty, apparatus comprising:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region;

a display device connected to the image capture device and adapted to display images captured from the image capture device; and a processor adapted to cause overlay of one or more second markers in the images displayed by the display device such that, when one or more of the first markers shown in the displayed images are substantially aligned with one or more of the second markers overlaid in the displayed images, the acetabular cup impactor is oriented in the desired orientation.

According to another aspect, the present disclosure provides a method of positioning an acetabular cup impactor, comprising:

mounting an image capture device on one of an acetabular cup impactor and a patient's pelvic region, the acetabular cup impactor being moveable to a desired orientation relative to the patient's pelvic region for implantation of an acetabular cup;

using the image capture device to capture images of the other of the acetabular cup impactor and the patient's pelvic region, including one or more first markers positioned on that other of the acetabular cup impactor and pelvic region;

displaying the images captured from the image capture device on a display device connected to the image capture device; and overlaying one or more second markers in the images displayed by the display device such that, when one or more of the first markers shown in the displayed images are substantially aligned with one or more of the second markers overlaid in the displayed images, the acetabular cup impactor is oriented in the desired orientation.

In one embodiment, the image capture device is mounted or adapted to be mounted on the acetabular cup impactor, and the image capture device is adapted to capture images of the patient's pelvic region, including one or more first markers positioned at the patient's pelvic region. The apparatus may comprise a mount that is configured to engage both the image capture device and the impactor and releasably fix the positions of the image capture device and the impactor relative to each other. The mount may include two clamp portions, for example, adapted to clamp to the image capture device and the impactor, respectively.

In this embodiment, the one or more first markers may comprise one or more anatomical landmarks. For example, the one or more anatomical landmarks may comprise one or both of the anterior superior iliac spines. In one embodiment, the one or more first markers comprise a vector line extending between anterior superior iliac spines. The vector line may be an imaginary line between the anterior superior iliac spines or may be a line that is drawn on the patient's pelvic region. Alternatively, the vector line may be a line that is drawn on, or provided by an edge, channel or visual feature, of a marker element, e.g. a rod, bar or other device, which is connected to or positioned adjacent the pelvis.

The apparatus may comprise a tilt sensor. The tilt sensor may be fixed in relation to the acetabular cup impactor and/or the image capture device. The tilt of the impactor and/or image capture device can be determined as the image capture device moves, e.g. as a result of moving the acetabular cup impactor. The tilt may be measured relative to a horizontal plane, for example.

The image capture device, in addition to any one or more of the display device, the processor and the tilt sensor, may be comprised in a single electronic device, such as a smartphone, tablet computer, or similar. The electronic device may run a software program or software "app" adapted to control the display device, processor and/or tilt sensor in accordance with the apparatus and methods of the present disclosure.

The mount of the apparatus may be adapted to engage both the electronic device and the impactor and releasably fix the positions of the electronic device and the impactor relative to each other. The mount may include two clamp portions, for example, adapted to clamp to the electronic device and the impactor, respectively.

The desired orientation of the impactor may correspond to an optimum implantation orientation of the acetabular cup. The optimum orientation can be defined by angles of inclination (abduction) and/or anteversion, for example. The desired orientation may be a desired angle of anteversion or a desired angle of inclination or a desired combination of anteversion and inclination angles.

The processor may be adapted to receive orientation data related to the impactor. The orientation data may include desired orientation of the impactor, e.g. desired anteversion and/or inclination angles, and/or measured orientation data, e.g. measured anteversion and/or inclination angles. Based on the received orientation data, the processor may determine appropriate positions and/or orientations for the one or more second markers displayed in the images. A commonly desired anteversion angle is about 20° and a commonly desired inclination angle is about 45°. Nevertheless, depending on circumstances including the anatomy of the patient and preferences of the surgeon, the desired anteversion may be anywhere between 0° and 40°, or even −35° and 60°, and the desired inclination may be anywhere between 35° and 50, or even 25° and 60°.

According to one aspect, the present disclosure provides a method of guiding the positioning of an acetabular cup impactor in a hip arthroplasty procedure, the method being adapted for use with hip arthroplasty apparatus that comprises:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region; and a display device connected to the image capture device and adapted to display images captured from the image capture device; and a processor adapted to cause overlay of one or more second markers in the images displayed by the display device such that, when one or more of the first markers shown in the displayed images are substantially aligned with one or more of the second markers overlaid in the displayed images, the acetabular cup impactor is oriented in the desired orientation, the method comprising:

determining the position and orientation for the one or more second markers to be overlaid in the images displayed by the display device based on received orientation data including a desired angle of orientation of the acetabular cup impactor and a measured orientation angle of the acetabular cup impactor data.

In one embodiment, the received orientation data comprises a desired anteversion angle of the acetabular cup impactor and a measured inclination angle of the impactor. In another embodiment, the received orientation data comprises a desired inclination angle of the acetabular cup impactor and a measured anteversion angle of the impactor. In another embodiment, the received orientation data comprises desired anteversion and inclination angles of the acetabular cup impactor, and measured anteversion and inclination angles of the impactor.

In one embodiment, one or more of the measured angles may be obtained at least in part through a feature recognition process. For example, by determining the positioning of one or more of the first markers in the images, one or more of the angles of anteversion and inclination of the acetabular cup impactor may be measured.

Additionally or alternatively, the measured orientation angle may be obtained at least in part by the tilt sensor, particularly when the tilt sensor is fixed in position relative to the impactor. Since the tilt sensor may determine tilt with reference to a gravitational field, whether or not the tilt sensor provides a measured anteversion angle or measured inclination angle for the impactor can depend on the orientation of the patient during surgery, e.g. whether or not they are in a supine position or a lateral recumbent position.

In one embodiment, the tilt sensor may provide measurements of one of the anteversion angle and the inclination angle, which measurements can be presented and continually updated on the display (or on a different display). Following from this, the second markers may be used to guide orienting of the impactor with respect to the other one of the anteversion angle and the inclination angle only. Thus, the surgeon may orient the impactor so that it has one of the desired anteversion angle and the desired inclination angle by simply by observing changes in the displayed measurements from the tilt sensor and moving the impactor accordingly, and the surgeon may orient the impactor so that it has the other of the desired anteversion angle and the desired inclination angle by aligning one or more of the first markers shown in the displayed images with one or more of the second markers overlaid in the displayed images.

The step of determining the positions and/or orientations for the one or more second markers may be carried out by the processor.

In one aspect, the present disclosure provides software that causes the processor to perform the method of the preceding aspect. The software may cause the processor to perform the method of the preceding aspect when installed on an electronic device comprising the processor.

As indicated, the processor may be comprised in an electronic device such as a smartphone, tablet computer, laptop computer, personal computer or otherwise. The electronic device may comprise other features of the apparatus described above, such as the image capture device, display device and/or tilt sensor. The software may take the form of application software (e.g. an "app"), which may be downloadable from a media library such as iTunes™ or Android™ media libraries or otherwise.

Nonetheless, more generally, it will be recognised that processors or processing apparatus as disclosed herein may comprise a number of control or processing modules for controlling one or more components of the apparatus and may also include one or more storage elements, for storing desired angle data, measured angle data, orientation data, and/or patient data, etc. The modules and storage elements can be implemented using one or more processing devices and one or more data storage units, which modules and/or storage devices may be at one location or distributed across multiple locations and interconnected by one or more communication links. Processing devices may include tablets, smartphones, laptop computers, person computers personal digital assistants and other types of electronic devices, including systems manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

The processor may be adapted to adjust the orientation of the one or more second markers that are overlaid in the images displayed by the display device depending on the received orientation data. For example, the processor may be adapted to continually adjust the orientation of the one or more second markers that are overlaid in the images displayed by the display device depending on measured orientation data. The one or more second markers may comprise lines and the orientation of the lines (the angle that the lines extend across all or part of the displayed images) may be adjusted. In alternative embodiments, the one or more second markers may comprise dots, shapes, graduated shading and/or colouring, etc.

The orientation of one or more second markers that are overlaid in the images displayed by the display device may be at least partially dependent on the position in the images at which they are overlaid. For example, if one of the second markers is to be overlaid towards a lower region of the image, the lower region corresponding to a part of the image generated with respect to a lower portion or angle of the image capture device's field of view, the processor can be configured to orientate that second marker differently to an orientation that it would be overlay one of the second markers towards a higher region of the image, the higher region corresponding to a part of the image generated with respect to a higher portion or angle of the image capture device's field of view. The processor may be adapted to continually determine, for different positions of the image (e.g. at different distances from a central, 0°, axis of the image capture device's field of view), an appropriate orientation for a second marker that is to be overlaid at that position, depending on the desired and measured anteversion and/or inclination angles. Generally, this approach recognises that the field of view of the image capture device will necessarily cover a range of angles and therefore the orientation of items as seen within images captured by the image capture device, relative to the impactor on which image capture device is mounted, will partially depend on where in the field of view of the camera those items are positioned. The processor may be adapted to determine a plurality of different second marker orientation angles for multiple positions in the images at which second markers are to be overlaid, and the processor may be adapted to overlay the plurality of second markers in the images accordingly.

In one embodiment, the patient is in a supine position. The image capture device and the tilt sensor are mounted on the impactor. The tilt sensor is adapted to measure anteversion angles of the impactor and continually provide the measured anteversion angles to the processor. The processor is also adapted to receive a data input, or is pre-programmed, with the desired inclination angle of the impactor. Based in part on the continually measured anteversion angles and the desired inclination angle, the processor is adapted to continually determine an appropriate orientation of each one of a plurality of the second markers that are to be overlaid over the images, for different positions in the images (e.g. for different distances in the image from the central axis of the image capture device's field of view), and the processor is adapted to overlay the second markers in the images accordingly. Since the appropriate orientation for the second markers will change depending on the tilt of the impactor (the measured anteversion), the orientation of the second markers in the images may change substantially in 'real time' as the surgeon moves the impactor. Meanwhile, the processor is adapted to present the measured anteversion angle on the display and continually update the display as the measured anteversion angle changes.

In this embodiment, when at least one first marker visible in the image is brought substantially in alignment with its nearest second marker or second markers, the impactor will be oriented with substantially the desired inclination angle. At the same time, the desired anteversion angle can be achieved by observing the measured anteversion angle presented on the display, and moving of the impactor accordingly.

In an alternative embodiment, the patient is in a lateral recumbent position. The image capture device and the tilt sensor are mounted on/fixed to the impactor. Thus, the tilt sensor, in contrast to the preceding embodiment, is adapted to measure inclination angles of the impactor and continually provide measured inclination angles to the processor. The processor is also adapted to receive a data input, or is pre-programmed, with the desired anteversion angle of the impactor. Based in part on the continually measured inclination angles and the desired anteversion angle, the processor is adapted to continually determine an appropriate orientation of each one of a plurality of the second markers that are to be overlaid over the images, for different positions in the images (e.g. for different distances in the image from the central axis of the image capture device's field of view), and the processor is adapted to overlay the second markers in the images accordingly. Since the appropriate orientation for the second markers will change depending on the tilt of the impactor (the measured inclination), the orientation of the second markers in the images may change substantially in 'real time' as the surgeon moves the impactor. Meanwhile, the processor is adapted to present the measured inclination angle on the display and continually update the display as the measured inclination angle changes.

In this embodiment, when at least one first marker visible in the image is brought substantially in alignment with its nearest second marker or second markers, the impactor will be oriented with substantially the desired anteversion angle. At the same time, the desired inclination angle can be achieved by observing the measured inclination angle presented on the display, and moving of the impactor accordingly.

In an alternative embodiment, the image capture device is mounted or adapted to be mounted on the pelvic region, e.g. on the pelvic bone, and the image capture device is adapted to capture images of the acetabular cup impactor, including one or more first markers positioned on the acetabular cup impactor. The apparatus may comprise a mount that is configured to engage both the image capture device and the pelvic region and releasably fix the positions of the image capture device and the pelvic region. The mount may include two clamp portions, adapted to clamp to the image capture device and the pelvic region, respectively.

In this embodiment, the one or more first markers may comprise one or more features of the acetabular cup impactor and/or one or more navigation elements attached to the acetabular cup impactor. For example, the impactor may be generally elongate and may define a longitudinal axis and the one or more first markers comprise a vector line extending along the longitudinal axis. The vector line may be an imaginary line, a line that is drawn on the impactor, or a line provided by an edge, channel or other visual feature of the impactor. Additionally or alternatively, other types of markers may be used. For example, one or more circles, part-circles, ellipses, part-ellipses, spheres or other shapes may be provided in fixed positions relative to the impactor. Where a plurality of first markers is provided, the markers may be positioned at different distances along the longitudinal axis of the impactor, for example.

This embodiment may differ from one or more of the embodiments described previously in that it may not make use of a tilt sensor to continually determine one of the anteversion and inclination angles. Particularly when the image capture device and the tilt sensor are integrated into a single device, since the image capture device is mounted to the pelvic region, which remains substantially stationary relative to the gravitational field when the impactor is moved, a tilt sensor may be not be available for monitoring changes in anteversion or inclination of the impactor. Nonetheless, the tilt sensor may be used to determine the orientation of the pelvis, before, during and/or after surgery, as an alignment tool.

A calibration procedure may be employed in order to determine an appropriate position for one or second markers to be overlaid on the displayed images, such that when one or more of the first markers shown in the displayed images are substantially aligned with one or more of the second markers overlaid in the displayed images, the acetabular cup impactor is oriented in the desired orientation. The calibration procedure may be carried out to determine, generally, the pivot point of the impactor relative to the image capture device, the length of the impactor and/or the positions of the one or more markers on the impactor. Based on these details, the processor may determine where the one or more second markers should be overlaid in the images to guide positioning of the impactor to the desired orientation.

The calibration procedure may be performed with the impactor and acetabular cup engaged in the hip socket of the pelvic region and/or performed remotely from the pelvic region.

During the calibration procedure, the processor may overlay one or more third markers on the images, which third markers indicate one or more positions at which one or more of the first markers should be located during the calibration procedure. When positioned accordingly, a user action may be required to provide further information to the processor. For example, when one of the first markers is aligned with one of the third markers, a user may be required to identify on the display the location of a different one of the first markers and/or the location of the shaft of the impactor. The identification may be performed by touching the display (if a touch screen display is used) or moving and 'clicking' a visible cursor in the image. This process of alignment with a third marker and subsequent location identification may be repeated multiple times (e.g. 2, 3, 4 or more times), but with the one or more third markers positioned differently in the images in each instance.

In some embodiments, second markers may not be overlaid over the images and other types of indicia may be used. Indicia representing both the anteversion and inclination angles of the impactor may be displayed substantially in 'real time' on the display, for example, enabling a surgeon to move the impactor to the desired orientation based on observation of changes to the displayed angles.

Following from this, according to a one aspect, the present disclosure provides hip arthroplasty, apparatus comprising:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region;

a display device connected to the image capture device and adapted to display images captured from the image capture device; and a processor adapted to provide one or more indicia in the images displayed by the display device to guide the acetabular cup impactor to the desired orientation.

According to another aspect, the present disclosure provides a method of positioning an acetabular cup impactor, comprising:

mounting an image capture device on one of an acetabular cup impactor and a patient's pelvic region, the acetabular cup impactor being moveable to a desired orientation relative to the patient's pelvic region for implantation of an acetabular cup;

using the image capture device to capture images of the other of the acetabular cup impactor and the patient's pelvic region, including one or more first markers positioned on that other of the acetabular cup impactor and pelvic region;

displaying the images captured from the image capture device on a display device connected to the image capture device; and providing one or more indicia in the images displayed by the display device to guide the acetabular cup impactor to the desired orientation.

According to yet another aspect, the present disclosure provides a method of guiding the positioning of an acetabular cup impactor in a hip arthroplasty procedure, the method being adapted for use with hip arthroplasty apparatus that comprises:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region; and a display device connected to the image capture device and adapted to display images captured from the image capture device; and a processor adapted to provide one or more indicia in the images displayed by the display device to guide the acetabular cup impactor to the desired orientation, the method comprising:
 determining an orientation of the acetabular cup impactor data based at least on a positioning of the one or more first markers in the images; and
 based on the determined orientation, providing one or more indicia in the images displayed by the display device to guide the acetabular cup impactor to the desired orientation.

According to yet another aspect, the present disclosure provides hip arthroplasty apparatus comprising: an acetabular cup impactor moveable to a desired orientation relative to a patient's pelvic region for implantation of an acetabular cup; and an electronic orientation sensor transitionable between a first location on the patient's pelvic region and a second location on the acetabular cup impactor; a mating component configured to mate with a portion of the patient's pelvis in a predetermined orientation; wherein, at the first location, the orientation sensor is coupled to or integrated with the mating component and is adapted to record a reference orientation of the patient's pelvic region, and, at the second location, the orientation sensor is adapted to determine an orientation of the acetabular cup impactor relative to the reference orientation.

According to yet another aspect, the present disclosure provides a method of positioning an acetabular cup impactor, comprising: locating mating component at a first location on a patient's pelvic region, the mating component configured to mate with a portion of the patient's pelvic region at the first location, the mating component having coupled thereto an electronic orientation sensor, using the electronic orientation sensor located at the first location to record a reference orientation of the patient's pelvic region, transitioning the electronic orientation sensor from the first location to a second location on an acetabular cup impactor, the acetabular cup impactor being moveable to a desired orientation relative to the patient's pelvic region for implantation of an acetabular cup, and using the orientation sensor located at the second location to determine an orientation of the acetabular cup impactor relative to the reference orientation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments are now described with reference to the accompanying drawings, in which:

FIGS. 32a to 32c illustrate the use of the electronic device of FIG. 1 for aligning a femoral tunnel during ACL reconstruction surgery.

DESCRIPTION OF EMBODIMENTS

Figure 1:
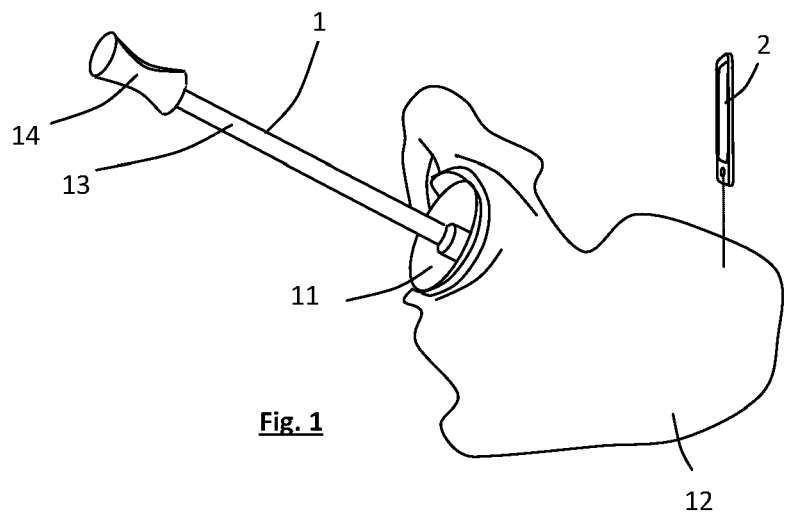
FIG. 1 shows apparatus according to an embodiment of the present disclosure with an electronic device at a first location.
Figure 2:
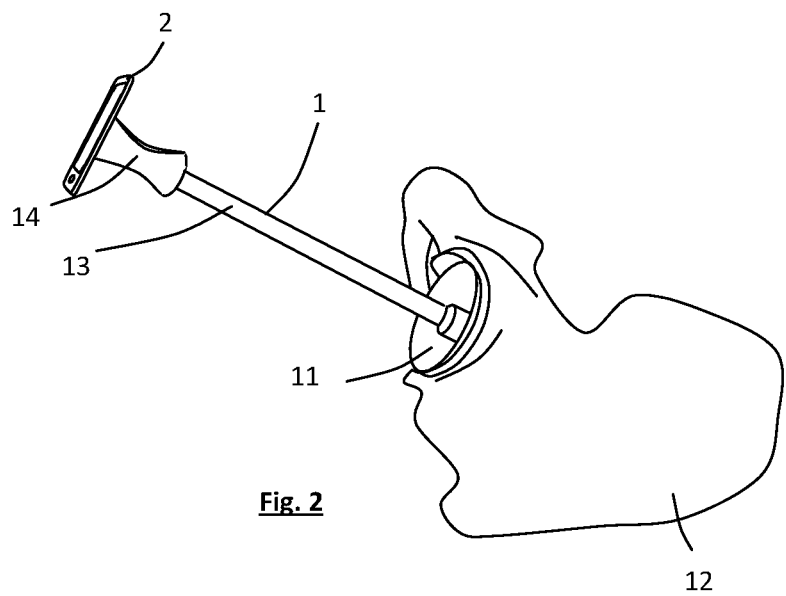
FIG. 2 shows the apparatus of FIG. 1 with the electronic device at a second location.

FIGS. 1 and 2 show apparatus according to an embodiment of the present disclosure. The apparatus includes an acetabular cup impactor 1, adapted to drive and implant an acetabular cup 11 into position at the acetabulum of a patient's pelvic bone 12, and an electronic device 2, the electronic device 2 being adapted to be located at a first location on the pelvic region (see FIG. 1) and subsequently located at a second location on the acetabular cup impactor 1 (see FIG. 2).

Figure 3:
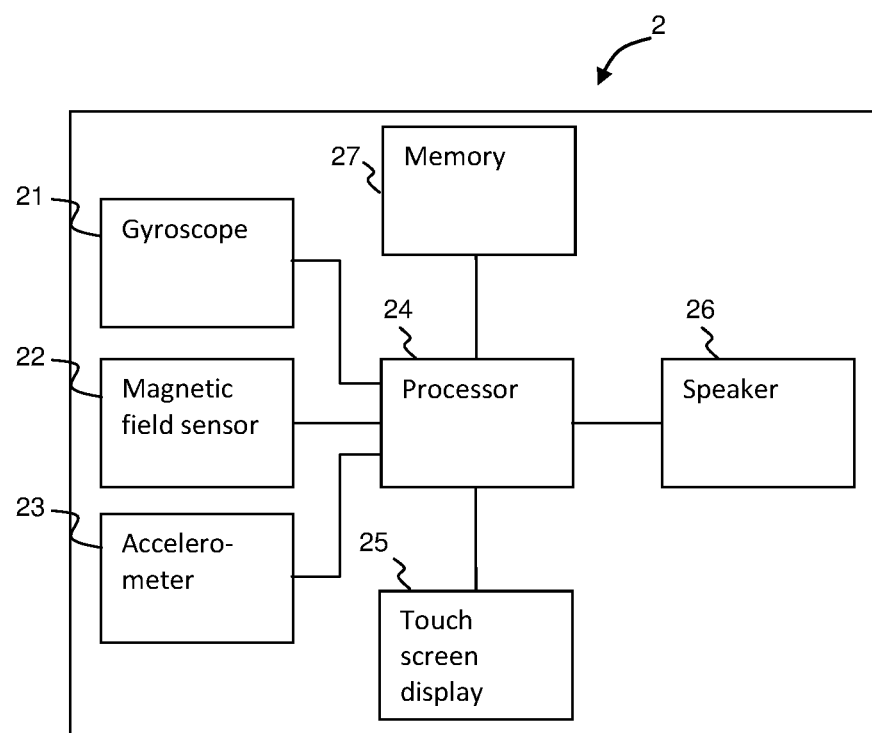
FIG. 3 shows a schematic view of elements of the electronic device of FIG. 1.

With reference also to FIG. 3, the electronic device 2 acts at least in part as an orientation sensor through inclusion of a gyroscope 21, a magnetic field sensor 22 and an accelerometer 23 connected to a processor 24. In alternative embodiments, one or more of these sensors may be excluded. For example, the accelerometer 23 may be excluded or otherwise. The electronic device 2 further includes an input device connected to the processor 24 that is in the form of a touch screen display 25, which touch screen display 25 also provides an output device in conjunction with a speaker 26. A memory 27 is provided for data storage and retrieval. In this embodiment, the electronic device 2 is a Smartphone, e.g. an iPhone™, although a variety of different electronic devices may be used. Further, the sensors, processor, input and output devices need not be integrated into a single device. For example, in one embodiment, the display and speaker may be maintained at a location that is remote from the pelvic region and impactor, and may communicate with the processor 24 via wires or wirelessly.

The acetabular cup impactor 1 includes a shaft 13 extending distally from the acetabular cup/pelvic region, and a handle 14 at the distal end of the shaft. In this embodiment, when at the second location as shown in FIG. 2, the electronic device 2 is releasably fixed to the distal end of the handle 14 such that planar face of the electronic device, which includes the display 25, is fixed at an orientation that is substantially orthogonal to the impactor shaft 13. A mount (not shown) is adapted to clamp the electronic device 2 to the handle 14. The electronic device 2 may be encased in a plastic covering. The plastic covering may hermetically seal the electronic device 2.

The gyroscope 21, magnetic field sensor 22 and accelerometer 23 of the electronic device provide in combination with the processor 24 an orientation sensor that can track orientation of the electronic device 2, and hence the acetabular cup impactor 1 when mounted thereon. By sensing movement of the electronic device 2 within the surrounding gravitational and magnetic fields, and optionally also acceleration and deceleration of the device 2, changes in orientation about three orthogonal axes of a coordinate system can be monitored.

In use, as part of a calibration process, the electronic device 2 is mounted at the first location on the pelvic region of the body as shown in FIG. 1. In particular, in this embodiment in which the patient is in a supine position, it is mounted so that its bottom edge substantially lines up with a vector line extending between right and left anterior superior iliac spines (ASIS) of the pelvic bone 12, also referred to herein as the "transverse vector" of the pelvis. Additionally or alternatively, a different edge and/or other feature of the device 2 such as an extension member 202 can be aligned with the transverse vector T. Equally, the electronic device may be mounted so that an edge is at a different angle to the transverse vector, such as at a 45 degree angle. In any case, the alignment may be carried out visually by the surgeon and/or by positioning the device 2 relative to a guide (not shown) that may be extended partially or entirely between the left and right ASISs 1201 of the patient. By mounting the electronic device 2 at a particular orientation relative to the pelvis, the device 2 can determine its orientation relative to an anatomical reference frame so that subsequent changes in orientation and movement of the device 2, for example, into the second position, can be determined. The anatomical reference frame may include (i) a transverse axis, which generally extends parallel to the transverse vector of the pelvis, (ii) a longitudinal axis, which generally extends in a superior-inferior direction of the patient assuming the patient is lying down, and (ii) an anteroposterior axis which generally extends between anterior and posterior sides of the patient, the transverse, longitudinal and anteroposterior axes being perpendicular to one another.

In FIG. 1 and subsequent Figures, for simplicity, the pelvic bone of the patient is represented independently of any other body parts or body tissue. In practice, other body parts and body tissue would, of course, be present.

Figure 4:
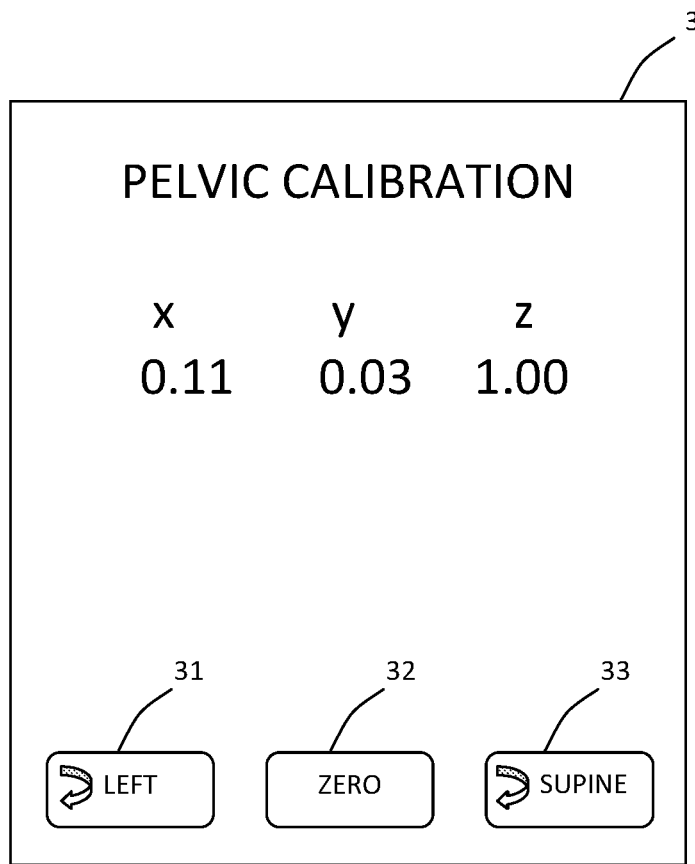
FIG. 4 shows a pelvic calibration display screen from the electronic device of FIG. 1.

When the electronic device 2 is at the first location, the display 25 is adapted to display a pelvic calibration screen 3 as represented in FIG. 4. Three touch-screen buttons are provided on the screen 3. One of the buttons 31 enables input of the hip side of the patient, in particular so that a clinician or other user can indicate if the hip replacement is being carried out in relation to the left or right hip. Another of the buttons 33 enables input of the positioning of the patient, in particular so that the clinician or other user can indicate if the patient is in a supine or a lateral orientation. In some embodiments, however, the electronic device 2 uses gravity measurements from the magnetic field sensor 22 to detect whether the patient is in a supine or lateral position. Finally, a zero button 32 is provided, which is to be pressed once the positioning of the patient and hip side have been inputted, and once the electronic device 2 is securely positioned at the first location (i.e. at the appropriate calibration position). When the zero button 32 is pressed, the electronic device 2 records its orientation, and hence the orientation of the pelvic region, and uses this as a reference orientation against which all subsequent changes in orientation of the electronic device 2 are compared.

Figure 5:
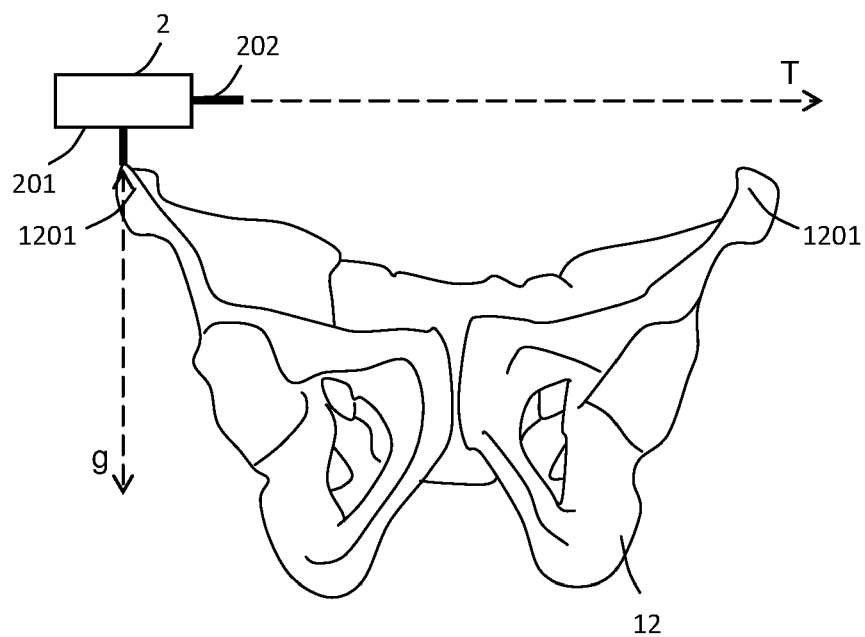
FIG. 5 shows the electronic device of FIG. 1 mounted to the pelvis of a patient.

In the above embodiments, the device 2 is aligned relative to the transverse (ASIS) vector and so its orientation relative to the transverse (ASIS) vector is known. An anteroposterior axis can then be determined by measuring a vector of gravity g using the magnetic field sensor 22 of the device 2. When the pelvis is in a supine orientation, as shown in FIG. 5, the vector of gravity g measured by the magnetic field sensor 22 will be substantially perpendicular to the transverse vector T between left and right ASISs 1201, and will be representative of the anteroposterior axis of the patient provided the surface upon which the patient is lying is substantially perpendicular to the gravity vector. In such cases, the gravity vector g and the transverse vector T may be recorded by the electronic device 2 and used by the electronic device to determine a longitudinal vector, which will necessarily extend perpendicularly to both the transverse and gravitational vectors T, g. In some instances, due to asymmetries in the pelvic bone, the transverse (ASIS) vector may not be exactly perpendicular to the gravity vector measured by the magnetic field sensor 22. In such circumstances, the angle between the two vectors (or the difference between the angle and 90°) may be stored and/or used to correct for those pelvic asymmetries. In any case, the 'zero' orientation of the device 2 at the time of calibration can be calculated relative to the longitudinal axis of the patient as well as the transverse axis, leading to improved accuracy in orientating the acetabular cup.

To correct for the above-mentioned discrepancy of measured angles of the transverse (ASIS) vector and the gravity vector, a vector perpendicular to both vectors may be determined by calculating the cross product of the gravity vector and the ASIS vector. This calculated vector will be parallel to the longitudinal axis of the patient (longitudinal vector). The cross product of the calculated longitudinal vector with the gravity vector will then give a "corrected ASIS vector".

Figure 6:
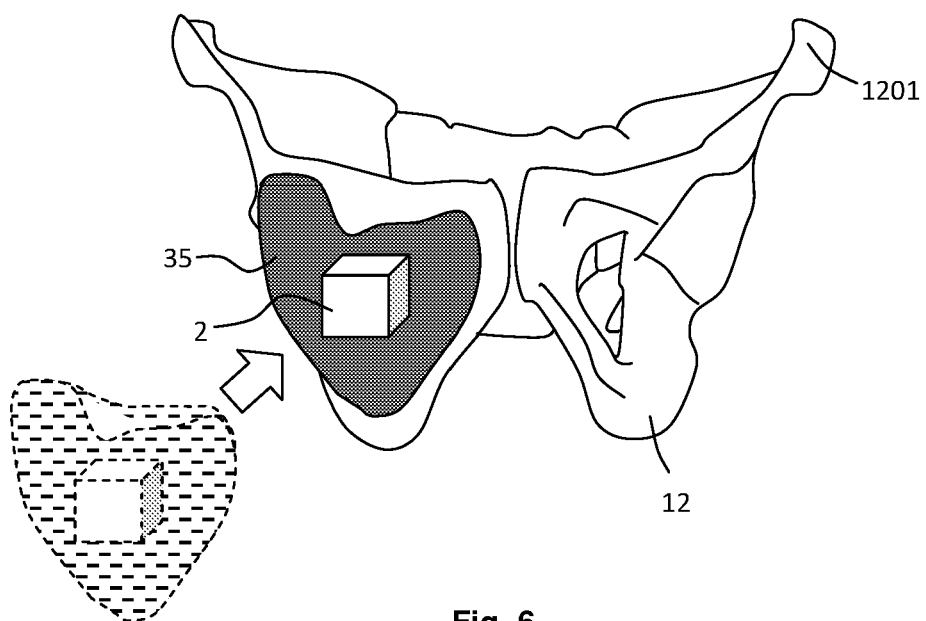
FIG. 6 shows an electronic device coupled to a temporary implant molded to conform with the interior of an acetabulum.

A variation of the above described alignment process is shown in FIG. 6. In this embodiment, the device 2 is coupled to or integrated with a temporary implant 35 molded to conform with the interior of the acetabulum. The implant 35 may be inserted into the acetabulum and, because the orientation of the device 2 relative to the implant 35 is known, the orientation of the device 2 relative to the pelvis is also known. Thus, a frame of reference can be calculated from orientation data measured by the device 2. With the implant 35 inserted in the acetabulum, a zero (or reference) orientation of the device can be measured. All subsequent changes in orientation of the electronic device 2 may then be compared with this reference orientation.

It will be appreciated that the implant 35 must be removed from the acetabulum before further operative steps are taken to prepare the acetabulum (reaming) and fit the acetabular prosthetic (cup). To maintain a frame of reference for the pelvis, being measured by the device 2, after recording a zero orientation at the device 2 and before any further operative steps are taken, the device 2 may be removed from the acetabulum and fixed relative to a different area of the pelvis out of the way of the acetabulum, for example, an ASIS of the pelvis. By recording the orientation translation of the device 2 from the acetabulum to the ASIS (or other pelvic region), the three dimensional frame of reference can be maintained If the device 2 is integral to the implant 35, the whole unit (implant 35 and device 2 may be moved in the above process. Otherwise, the device 2 may be moved and the implant 35 discarded.

As mentioned above, the implant 35 is manufactured to conform with the interior of the acetabulum. In some embodiments, the implant 35 may be manufactured to exactly match the anatomy of a particular patient's acetabulum. To do so, a three-dimensional (3D) scan of the patient's pelvic region may be performed and the implant 35 manufactured based on the scan of the patient's acetabulum. The implant 35 may be manufacture using additive manufacturing techniques (e.g. 3D printing) or the like.

In the above embodiments, the implant 35 is configured to mate with the acetabulum. In other embodiments, the implant 35 may be manufactured to conform with another part of the pelvic anatomy. If the chosen pelvic region is out of the way of the surgical area, the step of removing the implant prior to performing the steps of preparation and implantation may not be required. In such circumstances, the reference orientation measured by the device 2 forms the basis of the frame of reference of the pelvis for acetabular cup orientation.

In embodiments described above, accurate positioning of the electronic device 2 relative to the vector line between right and left ASISs 1201 of the pelvis 12 is required to ensure the accuracy of subsequent measurements of orientation of the acetabular cup impactor 1 when the electronic device is placed in the second position on the end of the impactor 1. However, inaccurate positioning of the electronic device relative to the pelvis may lead to inaccurate estimation of the position of the device 2 when translate into the second position at the end of the cup impactor 1. The following techniques reduce the effect on calibration of inaccurate mounting of the device 2 on the pelvis.

Figure 7A:
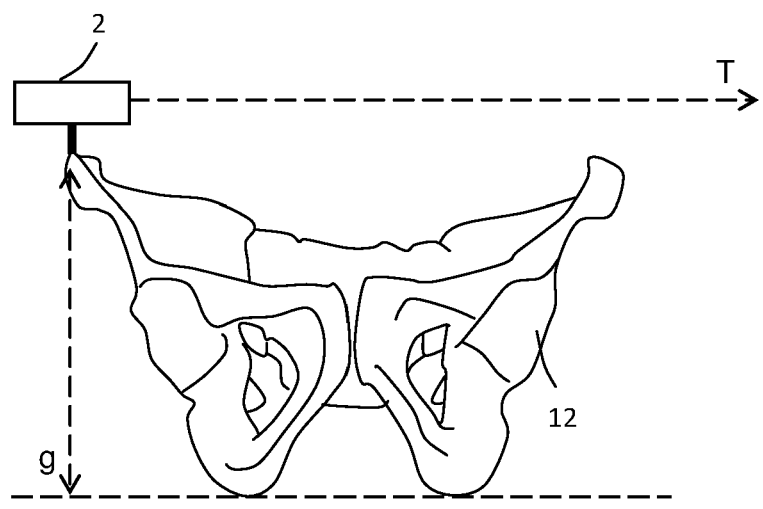
FIGS. 7a to 7c show rotation of the pelvis shown in FIG. 5 about a longitudinal axis of the patient.
Figure 7B:
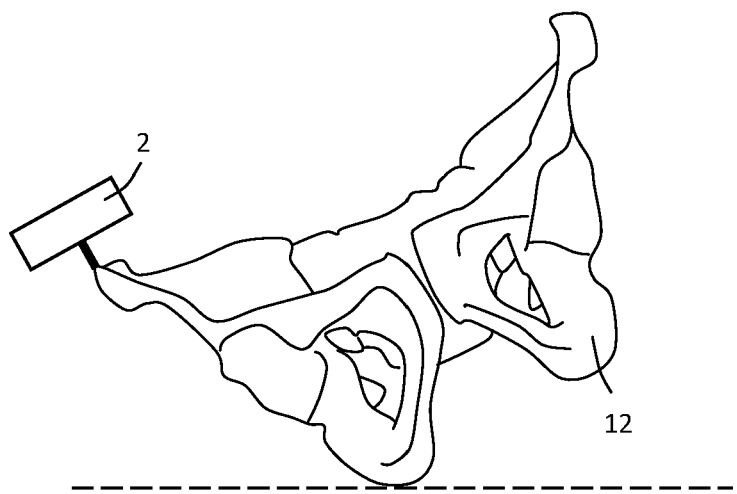
Figure 7C:
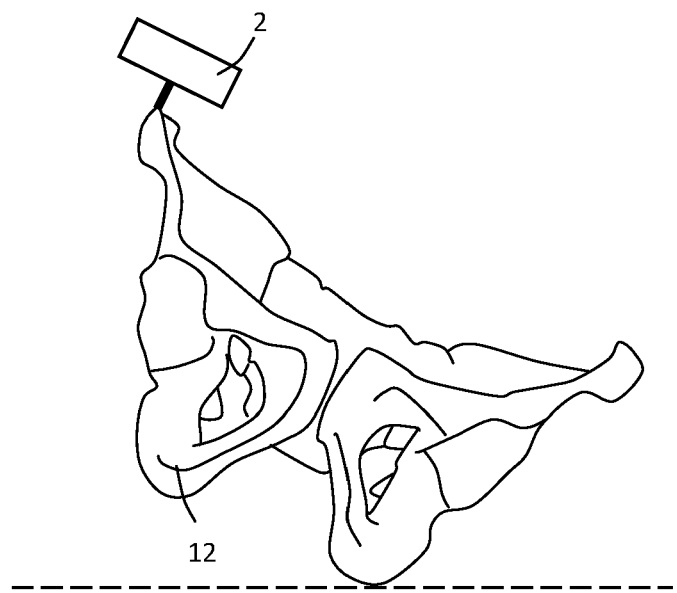

With reference to FIGS. 7a to 7c the device 2 is shown attached to a patient's pelvis 12, the device having an unknown or non-exact orientation relative to the pelvis 12. The vector of gravity g may be measured by the magnetic field sensor 22 when the patient is in a supine (or prone) position on a flat surface as shown in FIG. 7a, the gravity vector corresponding to the anteroposterior axis of the pelvis. The patient is then rolled toward their right side as shown in FIG. 7b and toward their left side as shown in FIG. 7c (in no particular order). Such rotation is preferably performed by longitudinally rotating an operating table upon which the patient is lying so as to prevent any sagittal pelvic tilt which might occur if the patient was turned without back support. As the patient is rotated, the electronic device 2 measures and records its orientation relative to the gravitational vector. The collected data can then be used to calculate the axis of rotation of the patient's pelvis (the longitudinal vector). With knowledge of the longitudinal vector of the pelvis and the gravity vector (and therefore the anteroposterior axis of the pelvis), the transverse (ASIS) vector can be calculated, which vector will necessarily extend perpendicularly to both the longitudinal and anteroposterior axes. Thus, an anatomical reference frame of the patient and specifically of the patient's pelvis, which reference frame includes the anteroposterior axis, the longitudinal axis of the patient as well as the transverse axis can again be determined.

It will be appreciated that although in the example described above, the patient is rolled in two directions (e.g. onto their left side and their right side), this is not necessary for determining a longitudinal vector. In order to determine the longitudinal vector, the patient need only be rolled in one direction, i.e. between a starting position and a rolled position. It will be appreciated, however, that the greater the angle the patient is rolled through, the more accurate a determination of the longitudinal vector can be made.

In a variation of the above, the table could be rotated head down (Trendelenburg) and head up (reverse Trendelenburg) to define a transverse axis, and the longitudinal axis calculated accordingly.

In some circumstances, the measured longitudinal vector may not be exactly perpendicular to the measured gravity vector. For example, the surface upon which the patient is positioned may not be exactly perpendicular to the gravity vector. In which case, the angle between the gravity vector and the longitudinal vector (or the difference between the angle and) 90° may be stored and used in future calculations to correct for those pelvic asymmetries. For example, the cross product of the gravity vector and the longitudinal vector can be calculated to give the transverse vector. The cross product of the transverse vector and the gravity vector will obtain a corrected longitudinal vector. Alternatively, the cross product of the transverse vector and the longitudinal vector can be calculated to obtain a corrected anteroposterior vector.

Figure 8A:
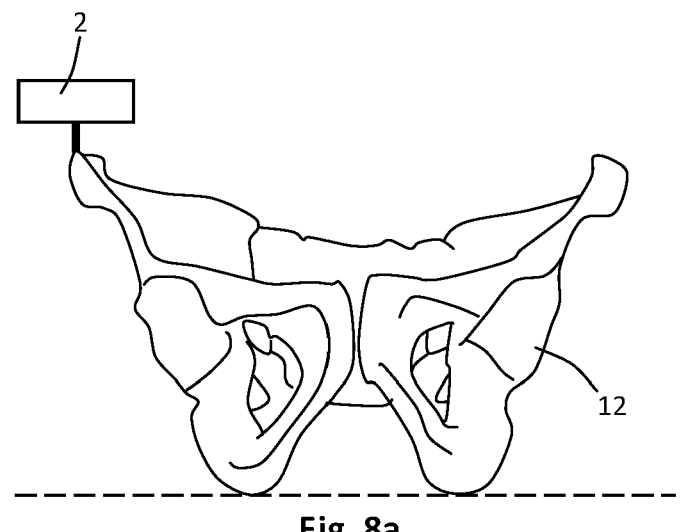
FIGS. 8a and 8b show the pelvis and electronic device of FIG. 5 in supine and lateral positions respectively.
Figure 8B:
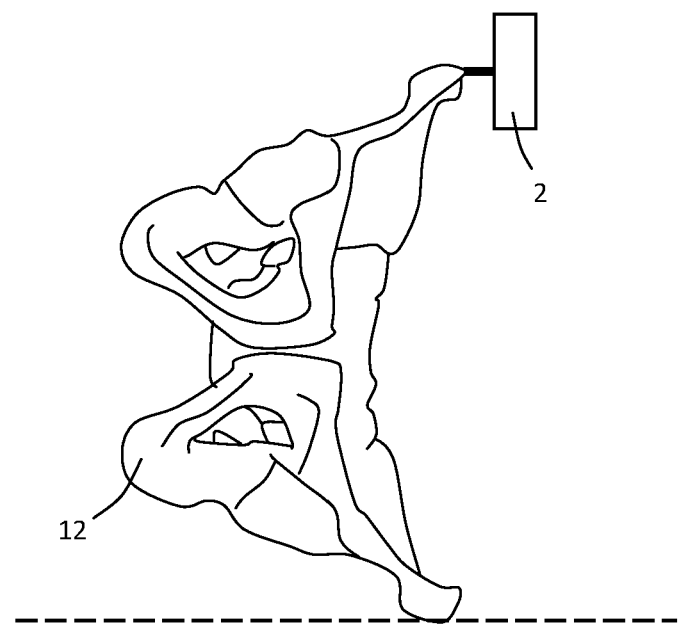

A further technique for determining the three-dimensional frame of reference for the electronic device 2 will now be described with reference to FIGS. 8a and 8b. Whilst the patient is in the supine position and with the electronic device 2 attached to the pelvis as shown in FIG. 8a, the gravity vector relative to the device is measured and recorded. When the patient is in the supine position, the gravity vector corresponds to the anteroposterior axis of the pelvis, provided the surface upon which the patient is lying is perpendicular to the gravity vector. The patient is then rotated 90° into a lateral position, as shown in FIG. 8b, and the gravity vector relative to the electronic device is again measured and recorded. When the pelvis of a patient is in the lateral orientation, the gravity vector should correspond directly to the transverse vector of the patient, provided the surface upon which the patient is lying is substantially perpendicular to the gravity vector. Accordingly, assuming that the gravity vector recorded while the patient is in a lateral orientation is parallel to the transverse vector of the pelvis, the longitudinal axis of the pelvis in both the supine and lateral positions can be determined relative to the device 2. Relative orientation of the device in three dimensions can be thus determined.

It will be appreciated that sagittal pelvic tilt of a patient may vary between supine and lateral orientation of the pelvis which in turn may introduce error, in particular, a discrepancy in the measured longitudinal vector in supine and lateral positions. The accuracy of the technique described above with reference to FIGS. 8a and 8b can therefore be further improved by taking an x-ray of the pelvis in a lateral position with a vertical beam and an x-ray plate beneath the patient. A determination of sagittal pelvic tilt in the lateral position may be made from the x-ray image. A discrepancy between the transverse vector of the pelvis and the gravity vector may also be determined from the x-ray image if, for example, the left and right ASISs are not aligned in the image. Information from the x-ray images concerning both sagittal pelvic tilt and ASIS alignment can then be used to correct or adjust reference axes. Correction may be performed manually by a clinician, or automatically.

The range of sagittal pelvic tilt of a patient may be used to determine the antiversion and inclination of implantation of an acetabular cup. For a patient with relatively high sagittal pelvic flexibility (high range of motion between maximum anterior and posterior pelvic tilts), the acetabular cup is preferably implanted with greater antiversion and reduced inclination than for a patient with relatively low sagittal pelvic flexibility (low or zero range of motion between maximum anterior and posterior pelvic tilts). Accordingly, in some embodiments, before the electronic device 2 is relocated from the first position but after a three dimensional reference orientation has been determined at the device 2, a physician may use the device 2 to record the sagittal pelvic flexibility of the patient. This may be done by manually bending and straightening the patient's legs whilst keeping the torso stationary. The value of sagittal tilt range for a patient may then be displayed and/or stored on the device 2. The sagittal tilt range value may be used to calibrate the output inclination/antiversion displayed to a user as described in more detail below.

Figure 9:
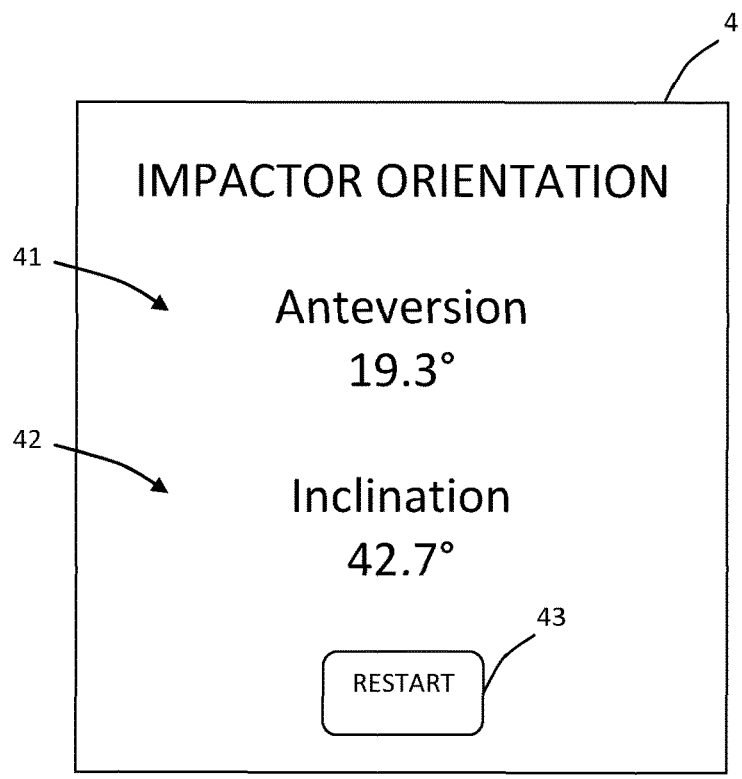
FIG. 9 shows an impactor orientation display screen from the electronic device of FIG. 1.

After calibration ('zeroing') of the electronic device 2 with respect to the anatomical reference frame, the electronic device 2 is transitioned from the first location on the pelvic region to the second location on the impactor 1, in particular at the distal end of the handle 14 as shown in FIG. 2, where it displays an impactor orientation screen 4 as represented in FIG. 9. As it transitions from the calibration position, the electronic device 2 continually monitors changes in its orientation relative to the reference orientation such that, when mounted on the handle 14, it immediately knows its orientation, and hence the orientation of the impactor shaft 13, relative to the reference orientation. The electronic device 2 can therefore display on the screen 4 the orientation of the impactor shaft 13 relative to the reference orientation (in terms of angle of anteversion 41 and angle of inclination 42 in this embodiment) and it can monitor and update the orientation on the screen, as it moves with the impactor 1 thereafter. Thus, the clinician or other user can observe the angles of anteversion and inclination in 'real-time' on the display, allowing him/her to move the acetabular cup impactor 1 to a desired orientation. The desired orientation may be an angle of 20° anteversion and 45° inclination or otherwise. Once completed, or if recalibration of the reference orientation is desired, a button 43 can be pressed to restart the procedure.

Example mathematics that may be employed in this or other embodiments is set forth below, where:
RI=radiographic inclination pelvic reference frame
RA=radiographic anteversion pelvic reference frame
AI=anatomic inclination pelvic reference frame
AA=anatomic anteversion pelvic reference frame
ri=radiographic inclination gravity reference frame
ra=radiographic anteversion gravity reference frame
ai=anatomic inclination gravity reference frame
aa=anatomic anteversion gravity reference frame
y'-y=yaw
r=roll
P=pelvic roll
Assuming no pelvic roll:
Yaw gives radiographic inclination (RI)
Roll gives radiographic anteversion (RA)
To convert to anatomic anteversion (AA) and anatomic inclination (AI) per Murray (D. W. Murray: The definition and measurement of acetabular orientation. *J Bone Joint Surg* [*Br*] 1993; 75-B: 228-32):
Tan(AA)=Tan(RA)/Sin(RI)
Cos(AI)=Cos(RI)*Cos(RA)
Therefore:
Anatomic Anteversion=arctan(tan(r)/sin(y'-y))
Anatomic Inclination=arcos(cos(y'-y)*cos(r))
If there is pelvic roll 'yaw' is calculated about a vertical axis that has rolled and roll calculated against the same axis.
Supine position with pelvic roll to the right in a right hip:
AA-P=aa
AA=aa+P
AI=ai
ra=r
ri=y'-y
Cos(AI)=cos(ai)
=Cos(ri)*Cos(ra)
AI=arccos(cos(y'-y)*cos(r))
AA=arctan(tan(r)/sin(y'-y))+P
And for a left hip:
AI=arccos(cos(y-y')*cos(r))
AA=arctan(tan(r)/sin(y-y'))−P.

Figure 10:
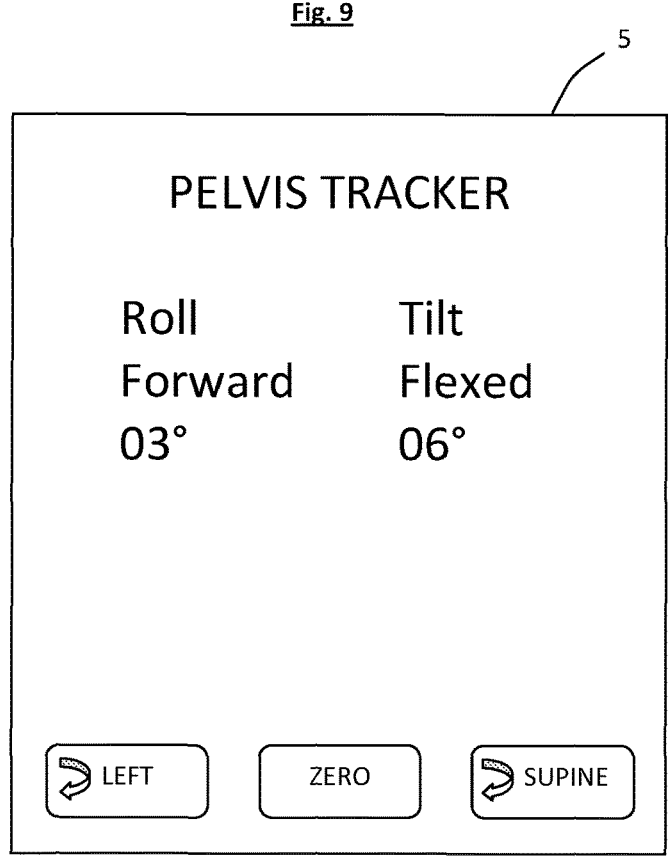
FIG. 10 shows a display screen from an electronic device used in another embodiment of the present disclosure.

In another embodiment of the present disclosure, the apparatus described above with reference to FIGS. 1 to 4 is adapted for use in tracking changes in orientation of the pelvic region during surgery. An electronic device is mounted to the pelvis, e.g. as represented in FIG. 1. However, after carrying out a calibration process as described with reference to FIG. 4, the electronic device 2 is maintained in position on the pelvic region and is used to track motion of the pelvic region in at least two rotational axes (pitch (tilt) and roll) or preferably three rotational axes (pitch, roll and yaw). The device 2 is adapted to display a pelvis tracking screen 5 as represented in FIG. 10, which presents the current orientation of the pelvis substantially in 'real-time' during the surgical procedure. The electronic device 2 is adapted to record the pelvic movement in the memory 27 throughout the surgical procedure. In one embodiment, predetermined limits on the degree of motion of the pelvis are inputted by the clinician into the electronic device 2, and an audible signal using the speaker 26 or other type of alarm is provided as a warning when these limits are exceeded.

Figure 11:
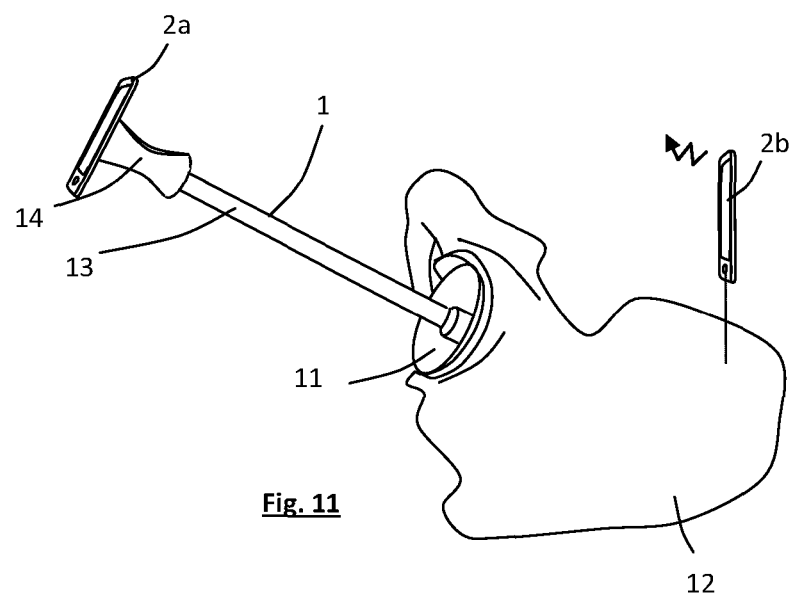
FIG. 11 shows apparatus according to another embodiment of the present disclosure.

In yet another embodiment, the approach described with respect to the two preceding embodiments is combined through the provision of two electronic devices 2a, 2b. Referring to FIG. 11, a first one of the electronic devices 2a is used as described above to record a reference orientation of the pelvic region prior to transitioning to the second location where it determines the orientation of the impactor 1 relative to the reference orientation. Further, a second one of the electronic devices 2b is used as described above to record a reference orientation of the pelvic region and is then maintained on the pelvic region to track changes in orientation of the pelvic region during surgery. The second electronic device 2b is adapted to wirelessly communicate with first electronic device 2a to provide information about changes in the orientation of the pelvic region, allowing correction of the reference orientation recorded by the first electronic device 2a to be made substantially in 'real-time'.

In a variation of the above approach using two electronic devices 2a, 2b, only one of the first and second electronic devices 2a, 2b need be initially registered with the pelvic region to record a reference orientation. For example, the second electronic device 2b may used as described above to record a reference orientation of the pelvic region. The first device 2a may then be positioned in a fixed location relative to the second device 2b, for example, attached to the first device, the pelvic region, another part of the patient, or the operating table upon which the patient may be lying. With the positions of the patient, the first device 2a and the second device 2b fixed, all three can then be rotated about any axis not parallel to the gravity vector, so long as that axis is known. Since the first and second devices 2a, 2b will be rotating about the same axis or axes, and since both devices 2a, 2b can measure the gravity vector, the first device 2a may be calibrated to the same coordinate system as that of the second device 2b and vice versa. Thus, the above approach offers a straightforward method of recording a common reference orientation for the two devices and the pelvic region. After registration of the two devices 2a, 2b, either device may remain attached to the pelvic region during surgery to record changes in orientation of the pelvic region as explained above. The other of the devices may then be moved to a position on the cup impactor 1 as described above.

Having regard for the above, it will be appreciated that the second electronic device 2b need not be registered with the pelvis region before registration of the first device 2a. In other words, recordation of the common reference orientation of the devices may be performed at the same time with a single synchronized rotation of the devices 2a, 2b.

Figure 12:
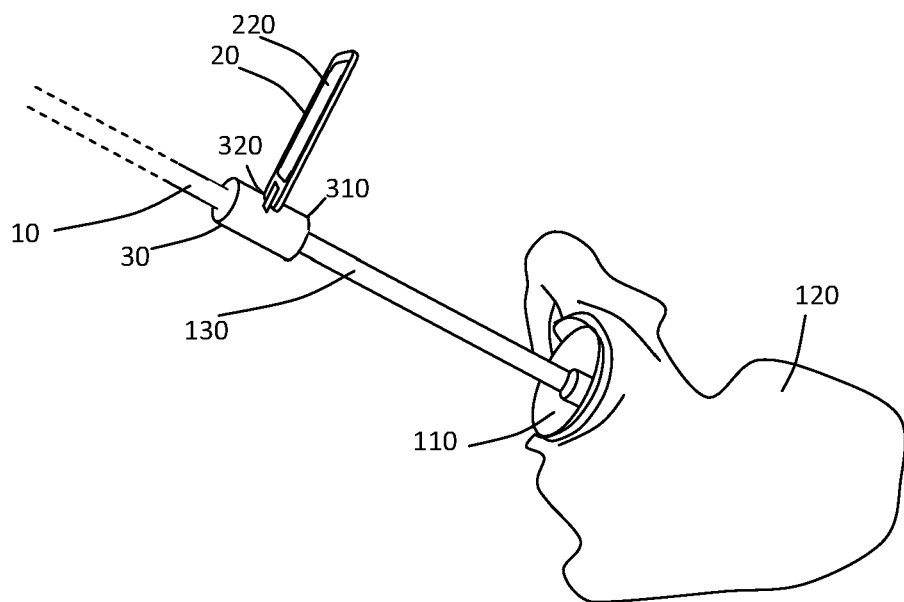
FIG. 12 shows apparatus according to another embodiment of the present disclosure.
Figure 14:
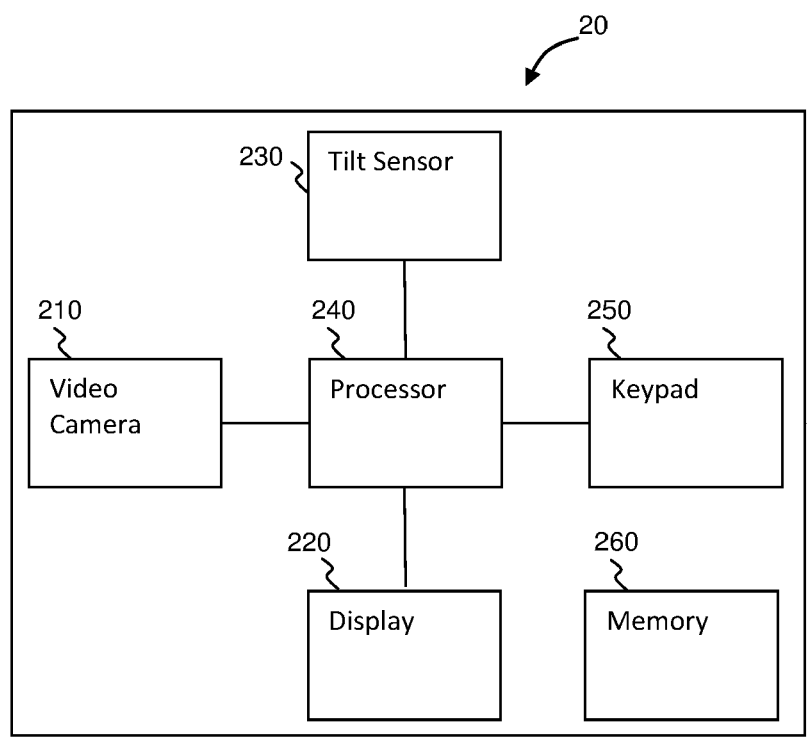
FIG. 14 shows a schematic view of elements of an electronic device used in the apparatus of FIG. 12.

FIG. 12 shows apparatus according to an embodiment of the present disclosure. The apparatus includes an acetabular cup impactor 10, adapted to drive and implant an acetabular cup 110 into position at the acetabulum of a patient's pelvic bone 120, and an electronic device 20, the electronic device 20 being mounted on the impactor 10. With reference also to FIG. 14, the electronic device 20 includes an image capture device in the form of a video camera 210, a digital display 220, a tilt sensor 230, a processor 240, a touch keypad 250 and a memory 260 for data storage and retrieval. In this embodiment, the electronic device 20 is a Smartphone, e.g. an iPhone™, although a variety of different electronic devices may be used. The camera 210, display 220, tilt sensor 230 and processor 240 need not be integrated into a single device 20, nor mounted on the impactor 10. For example, in one embodiment, the display and/or processor may be located remotely from the impactor 10.

The electronic device 20 is releasably fixed to the shaft 130 of the impactor 10 via a mount 30 such that the camera of the electronic device faces the pelvic bone 120 and, more generally, the pelvic region of the patient. The mount 30 is adapted to clamp to the shaft 130 of the impactor 10 through provision of a sleeve portion 310 that at least partially extends around the impactor shaft 130. The mount 30 is also adapted to clamp to the electronic device 20 through provision of one or more arms 320 that project from the sleeve portion 310 and abut opposing sides or edges of the electronic device 20. The electronic device 20 may be encased in a plastic covering. The plastic covering may hermetically seal the electronic device 20.

Figure 13:
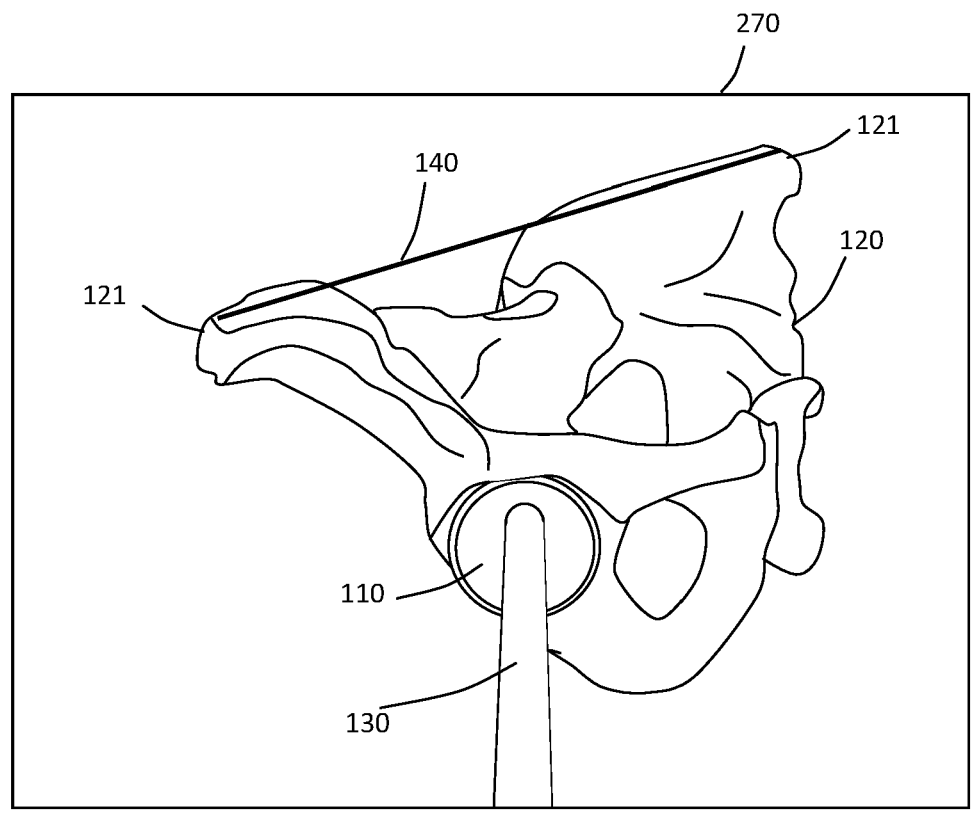
FIG. 13 shows an image of a pelvic region captured by a camera of the apparatus of FIG. 12.

The camera 210 of the electronic device 20 is adapted to sequentially capture a plurality of images of the pelvic region of the patient (i.e. video the pelvic region of the patient), and the images are presented, substantially in 'real time', on the display 220. The pelvis 120 includes a first marker 140 thereon, more particularly a vector line 140 extending between right and left anterior superior iliac spines (ASIS) 121 that is imagined or drawn on bone and/or tissue between ASIS 121. With reference to FIG. 13, which shows an example image (frame) 270 as presented on the display 220, the ASIS vector line 140 is represented in the image 270. In FIG. 12 and subsequent Figures, for simplicity, the pelvic bone 120 of the patient is represented independently of any other body parts or body tissue. In practice, other body parts and body tissue would, of course, be present.

The processor 240 of the electronic device 10 is adapted to receive orientation data related to the impactor 10 (and the acetabular cup 110). In this embodiment, the patient is located in a supine position, and the orientation data received by the processor 240 includes a desired inclination angle for the impactor and measured anteversion angles for the impactor. The desired inclination angle, which is 45° in this example, is input into the electronic device 20 using the touchscreen keypad 250. The anteversion angle is continually measured using the tilt sensor of the electronic device 20.

Figure 15:
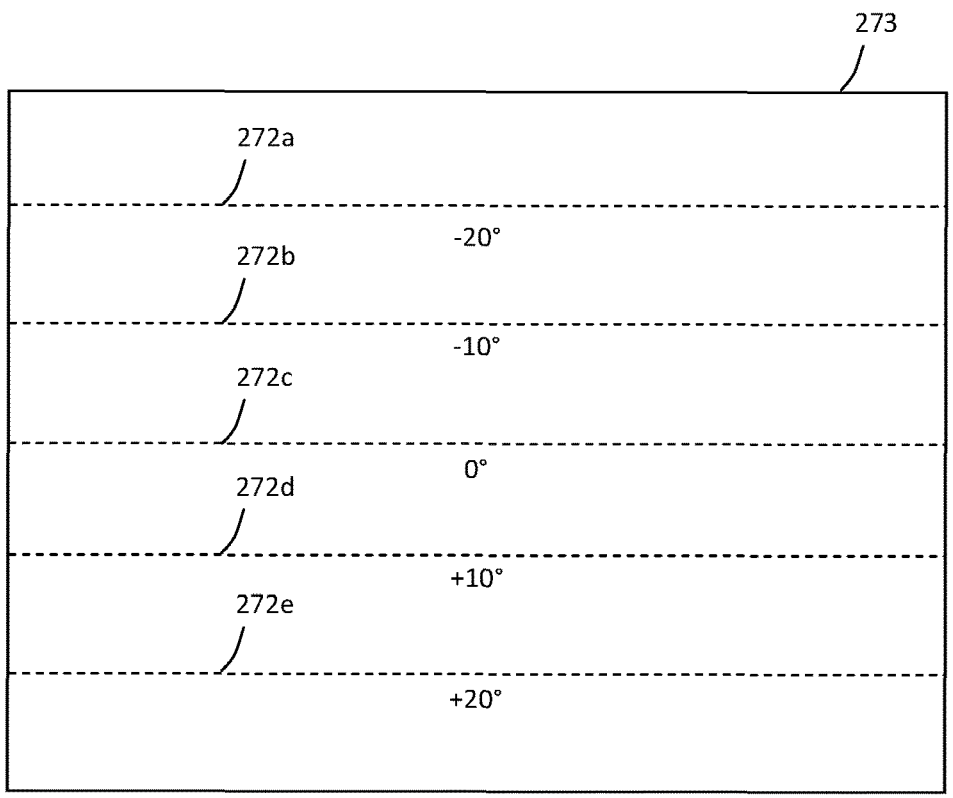
FIG. 15 shows an outline of the area covered by the image of FIG. 13, with guidelines positioned at different locations in the area, the guidelines being indicative of positions in the area that corresponding to 10° intervals within the field of view of the camera.

Based on the received orientation data, and with reference to FIGS. 14 and 15, the processor 240 is adapted to overlay one or more second markers, more particularly alignment lines 271a-e, in images 270a, 270b displayed by the display device 220 such that, when the ASIS vector line 140, as seen in the images, is substantially aligned with one or more of the alignment lines 271a-271e, the acetabular cup impactor 10 will be oriented at the desired angle of inclination.

In order to provide this guidance for the inclination angle, the processor 240 is adapted to determine the appropriate orientation for the plurality of alignment lines 271a-e, when overlaid at respective positions in the images 270. The appropriate orientation of the alignment lines 271a-e, when overlaid in the images, is partially dependent on the position in the images at which they are to be overlaid, due to the angular range of the field of view of the camera. This means that the orientations of items as seen within images, such as the ASIS vector line 140, are dependent not only on their actual orientation relative to the impactor 10, but on where in the field of view of the camera those items are positioned.

In this embodiment, the processor 240 is adapted to overlay five alignment lines 271a-e in the images 270a, 270b in accordance with equally spaced angular distances along the vertical axis of the field of view of the camera 210. In this embodiment, the camera 210 has a field of view of about 50° to 60° and the alignment lines are located, and their orientation determined, with respect to angular distances in the vertical axis of −20°, −10°, 0°, +10° and +20°, from the central horizontal axis of the camera's field of view. These angular distances are represented by guidelines 272a-e in FIG. 15, where FIG. 15 shows an outline 273 of the area covered by the image 270 of FIG. 13.

Using Equation 1, the processor 240 is adapted to determine for each angular distance (d) from the central horizontal line within the field of view of the camera, and for a measured anteversion angle (x) and a desired inclination angle (y), the angle (g) at which to orient alignment lines 271a-e that are to be overlaid in the images presented on the display.

$$\tan g = \tan(y) \cdot \sin(x+d) \qquad \text{Equation 1}$$

Figure 16:
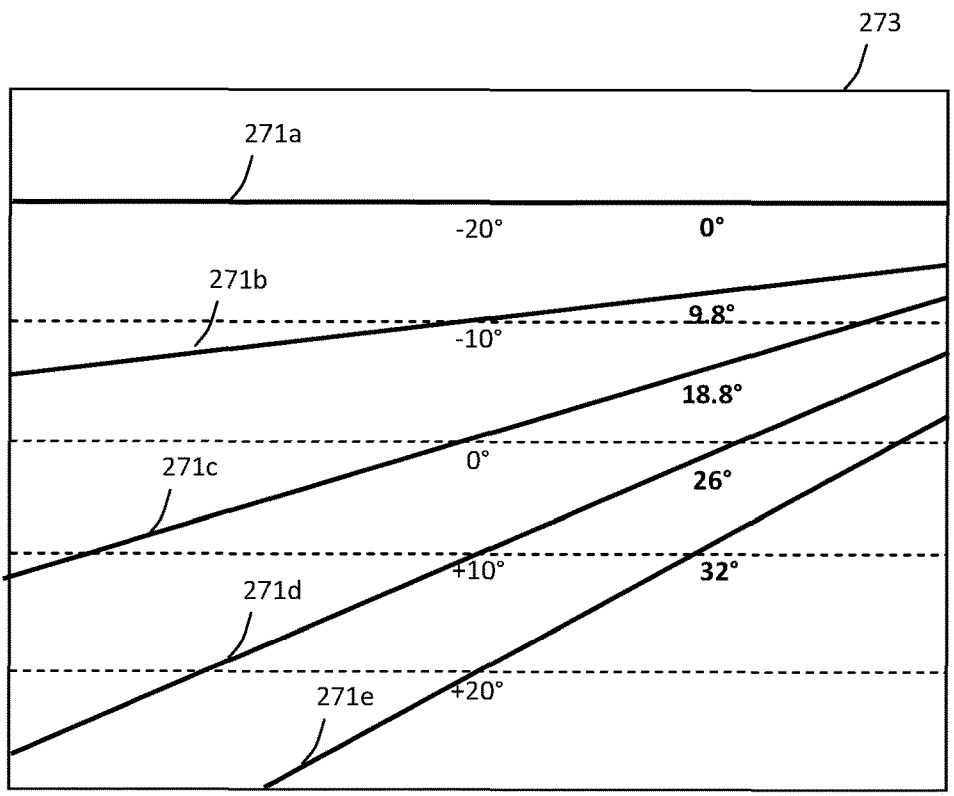
FIG. 16 shows a plurality of marker lines, each positioned with reference to one of the guidelines of FIG. 15, the marker lines being for guiding positioning of an acetabular cup impactor of the apparatus of FIG. 12.

Example orientations for the alignment lines 271a-e as determined using Equation 1 for each of the angular distances (d) are represented in FIG. 16, each alignment line 271a-e being overlaid next to a respective guideline 272a-272e. The orientations angles (g) can continually change as a result of the measured anteversion angle (x) changing as indicated above, and thus the alignment lines 271a-e can be seen to rotate within the screen as the impactor 1 is moved.

FIG. 16 shows a first image 270a as seen on the display by the surgeon, when the alignment lines 271a-271e have been overlaid by the processor 240. In the corner of the image 270a, the measured anteversion angle 274 is presented and continually updated as the impactor 10 moves.

The desired angle of inclination of the impactor 10 is achieved when the ASIS vector line 140 is substantially aligned with the nearest alignment line or lines 271a-e. In FIG. 16, the vector line 140 can be seen in image 270a positioned nearest the top two alignment lines 271a, 271b. The vector line 140 is substantially misaligned with these alignment lines 271a, 271b. This indicates that the impactor 10 is not at the desired angle of inclination. Furthermore, the anteversion angle 274 as presented on the display is at 23°, rather than a desired angle of 20°.

Figure 17:
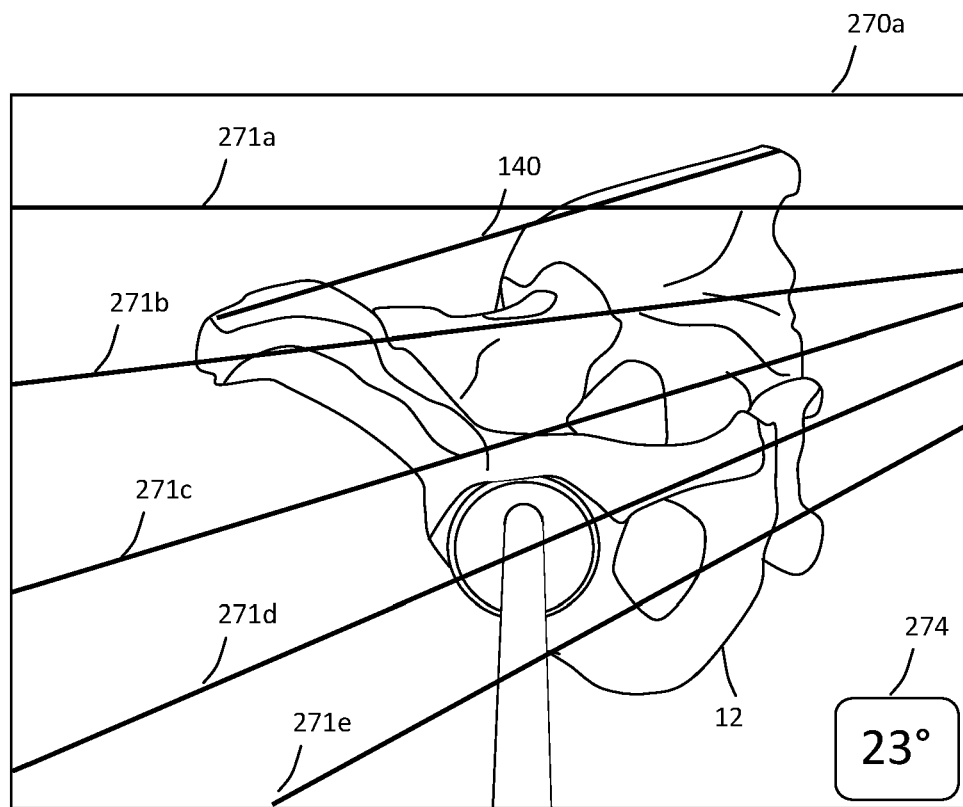
FIG. 17 shows the plurality of marker lines of FIG. 16 overlaid on the image of FIG. 10, with the acetabular cup impactor in a first position relative to the pelvic region.
Figure 18:
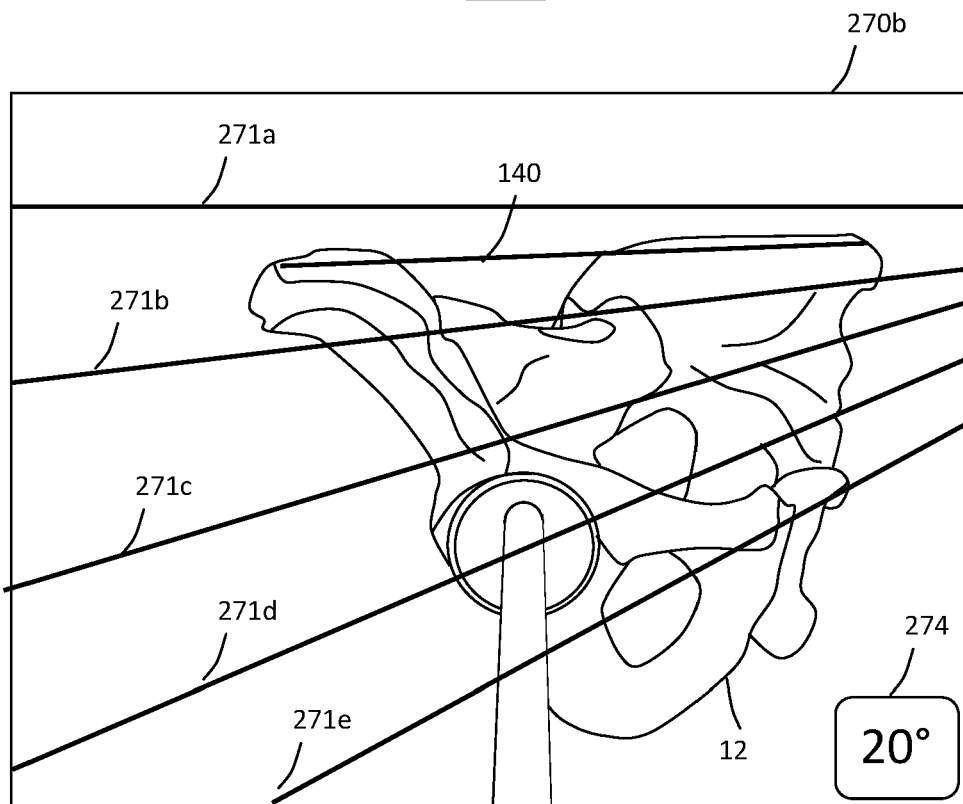
FIG. 18 shows the plurality of marker lines of FIG. 16 overlaid on the image of FIG. 10, with the acetabular cup impactor in a second position relative to the pelvic region.

However, through movement of the impactor 10, and observation of the display 220, the surgeon can move the impactor 10 to a position as represented in the image 270b of FIG. 17. In this image 270b, the vector line 140 is substantially aligned (i.e. substantially parallel) with the nearest alignment lines 271a, 271b and the anteversion angle 274 as presented on the display is at the desired angle of 20°. At this point, the desired orientation of the impactor 10, and thus the acetabular cup 110 connected to the impactor 10, is achieved.

As indicated, in this embodiment, the patient is in a supine position. However, the approach described above can be carried out, mutatis mutandis, with a patient in the lateral recumbent position. In this variation, the tilt sensor will provide the angle of inclination of the impactor, and the alignment lines will be used instead to arrive at the desired angle of anteversion. More particularly, when the ASIS vector line, as seen in the images, is substantially aligned with one or more of the alignment lines, the acetabular cup impactor will be oriented at the desired angle of anteversion.

Equation 2 can be utilised in place of Equation 1. In particular using Equation 2, the processor is adapted to determine for each angular distance (d) from a central horizontal line within the field of view of the camera, and for a measured inclination angle (y) and a desired anteversion angle (x), the angle (g) at which to orient alignment lines that are to be overlaid in the images presented on the display.

$$\tan g = \tan(x) \cdot \sin(y+d) \quad \text{Equation 2}$$

Figure 19:
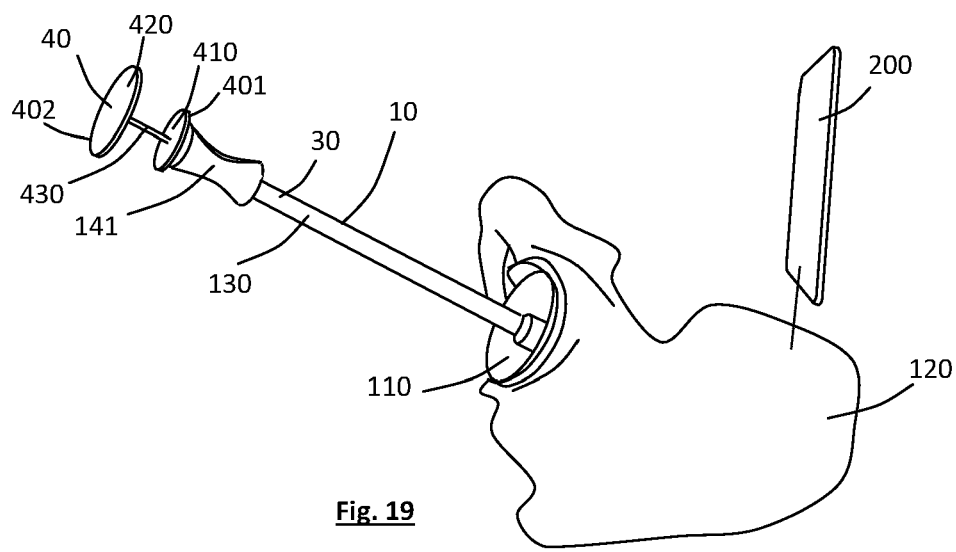
FIG. 19 shows apparatus according to another embodiment of the present disclosure.
Figure 21:
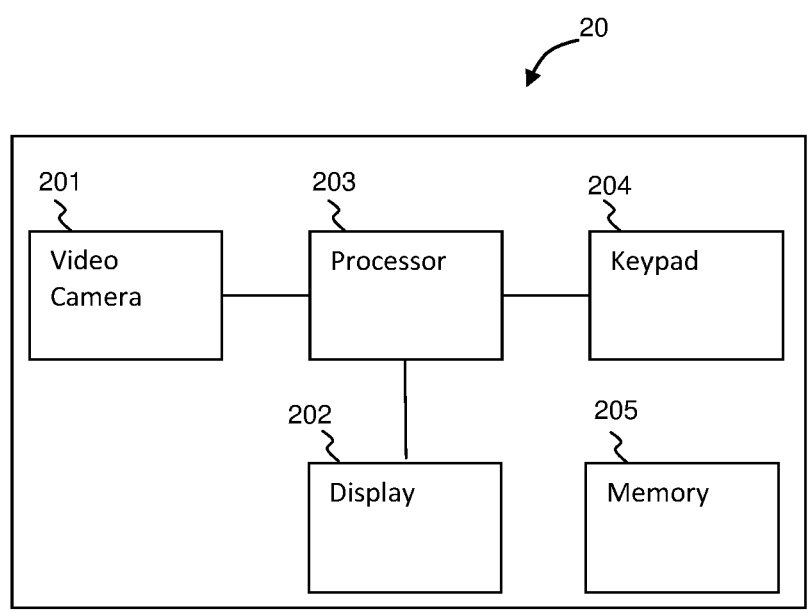
FIG. 21 shows a schematic view of elements of an electronic device used in the apparatus of FIG. 19.

FIG. 19 shows apparatus according to another embodiment of the present disclosure. The apparatus includes an acetabular cup impactor 10, adapted to drive and implant an acetabular cup 110 into position at the acetabulum of a patient's pelvic bone 120, and an electronic device 200, the electronic device 200 being mounted to the pelvic region, e.g. on the pelvic bone 120. With reference also to FIG. 21, the electronic device 200 includes an image capture device in the form of a video camera 201, a digital display 202, a processor 203, a touch keypad 204 and a memory 205 for data storage and retrieval. A tilt sensor may also be included. In this embodiment, the electronic device 200 is a tablet, e.g. an iPad™, although a variety of different electronic devices may be used. The camera 201, display 202, and processor 203 need not be integrated into a single device 200, nor all mounted on the pelvic region. For example, in one embodiment, the display and/or processor may be located remotely from the pelvic region.

The electronic device 200 is releasably fixed to the pelvic bone 120 or pelvic region via a mount (not shown) such that the camera 201 of the electronic device 200 faces the impactor 10. The electronic device 200 may be encased in a plastic covering. The plastic covering may hermetically seal the electronic device 200.

The camera 201 of the electronic device 200 is adapted to sequentially capture a plurality of images of the impactor 10 and the images are presented substantially in 'real time' on the display 202.

Figure 20:
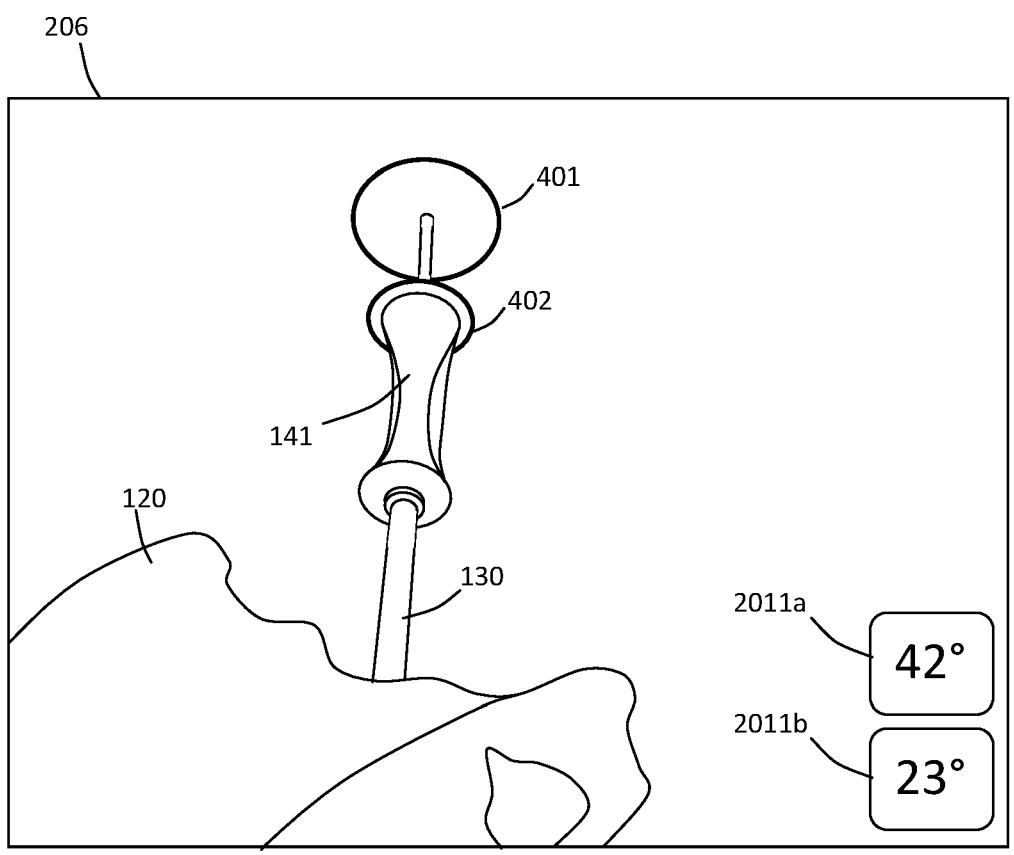
FIG. 20 shows an image of an acetabular cup impactor captured by a camera of the apparatus of FIG. 19.

A navigation element 40 in the form of two circular disks 410, 420, connected together by a spacer 430, is releasably mounted to the distal end of the impactor 10. The two disks 410, 420 are concentric and the centres of the disks 410, 420 are aligned with the longitudinal axis of the impactor 10. The disk 410 closest to the impactor 10 has a smaller diameter than the disk 420 furthest from the impactor 10. The edges 401, 402 of the disks define circles that provide two first markers. With reference to FIG. 20, which shows an example image (frame) 206 as presented on the display 202, the two first markers 401, 402 are visible in the image 206.

The processor 203 of the electronic device 200 is adapted to receive orientation data related to the impactor 10 (and the acetabular cup 110). In this embodiment, the patient is located in a supine position, and the orientation data received by the processor includes a desired inclination angle and a desired anteversion angle for the impactor. The desired inclination and anteversion angles, which are 45° and 20°, respectively, in this example, are input into the electronic device 200 using the touchscreen keypad 204.

Figure 22A:
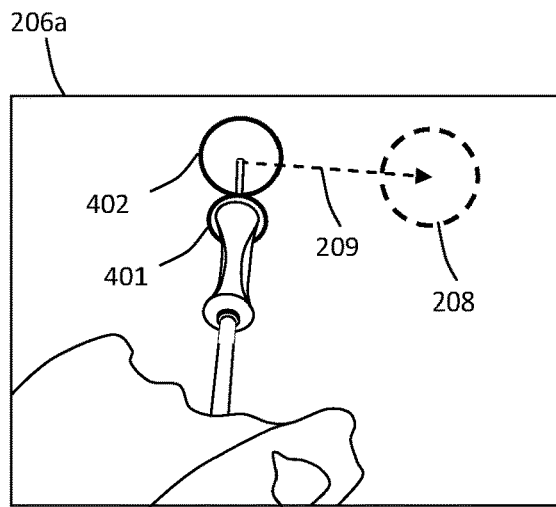
FIGS. 22a to 22d show calibration markers overlaid on images captured by the camera of the apparatus of FIG. 19.
Figure 22B:
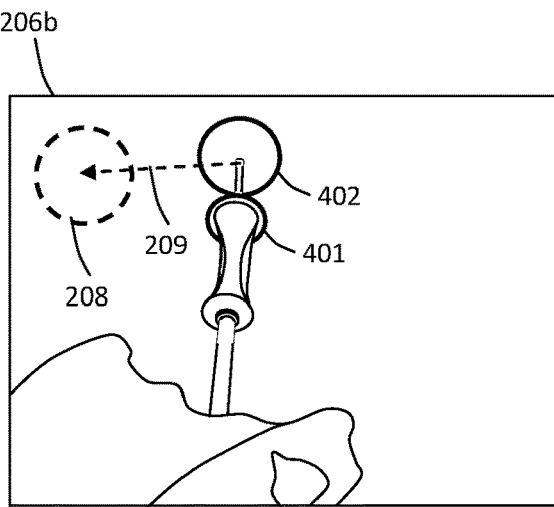
Figure 22C:
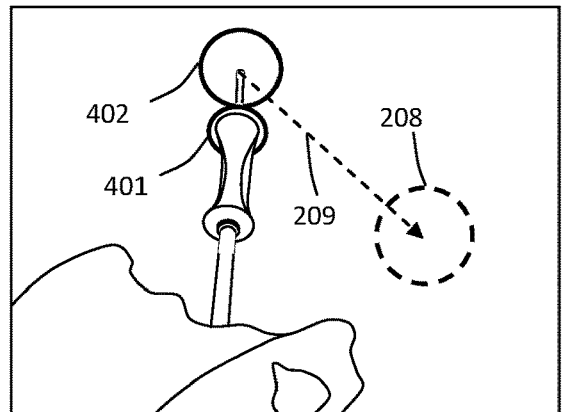
Figure 22D:
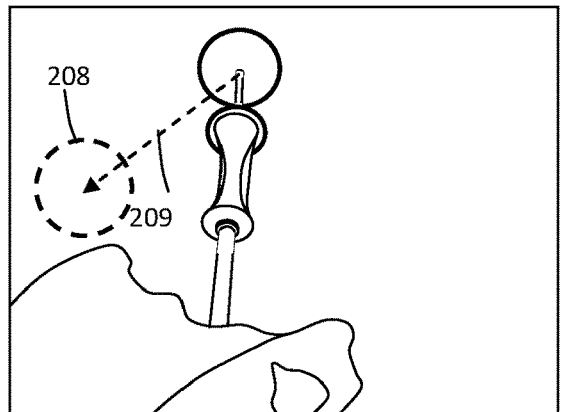

In this embodiment, a calibration procedure is performed to determine the pivot point of the impactor 10 relative to the camera 201 and the positions of the first markers along the longitudinal axis of the impactor 10. With reference to FIG. 22a, during the calibration procedure the processor 203 is adapted to overlay a third marker 208 in a first position in images 206a displayed by the display device 202. The impactor 10 is then moved by a surgeon, generally in a direction as indicated by arrow 209, such that one of the disks, in particular the larger disk 402 in this embodiment, is aligned with the third marker 208. Once aligned, the user is required to touch the screen, or 'click' a cursor on the screen, at the position in the image at which the other of the disks, in particular the smaller disk 401 in this embodiment, is located. This process is repeated for a number of different positions (e.g. second to fourth positions) of the third marker 209, as represented in images 206b-206d of FIGS. 22b to 22d. This enables a determination to be made of the exact and relative positions of the two first markers 401, 402 in the images 206a-206d, and through application of trigonometric functions, calibration data including the pivot position of the impactor relative to the camera, and the positions of the first markers along the longitudinal axis of the impactor, can also be determined.

Figure 23:
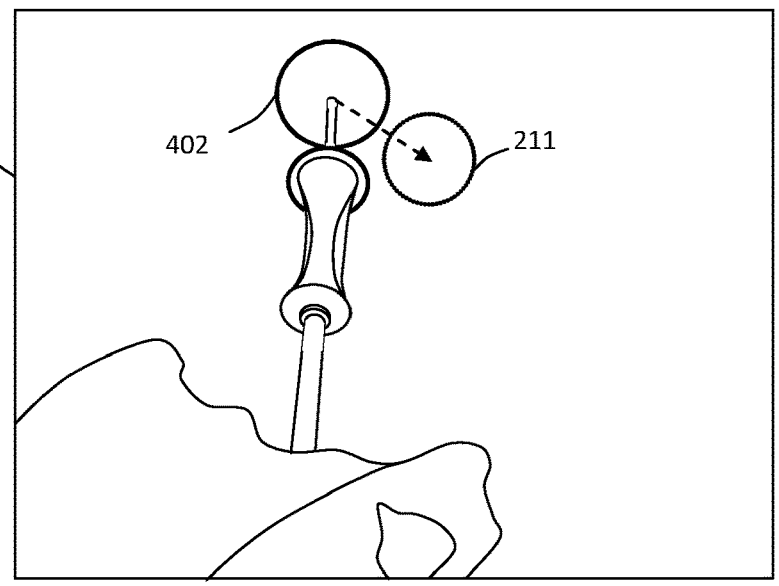
FIG. 23 shows an alignment marker overlaid on an image captured by the camera of the apparatus of FIG. 19.

Based on the calibration data and the received orientation data (i.e. the desired inclination and anteversion angles), the processor 203 is adapted to determine where in the displayed images a second marker 211 should be located to guide the impactor so that it has the desired inclination and anteversion angles. In this embodiment, with reference to FIG. 23, the processor 203 is adapted to overlay the second marker 211 in the images 206e displayed by the display device 202 such that, when the larger disk 402, as seen in the images, is substantially aligned with the second marker 211, the acetabular cup impactor 10 will be oriented at the desired orientation.

In a variation of this embodiment, the processor is adapted to use feature detection to determine the positions and shapes of the first markers 401, 402 within the images 206. The feature detection may be used in place of a user being required to touch or 'click' on the position of one of the first markers 401, in order to identify the position of that marker. Alternatively, feature detection may be used to remove the need for the calibration procedure entirely.

In more detail, to the extent that the centre of the camera 201 is misaligned with the longitudinal axis of the impactor 10, the first markers 401, 402 will appear as ellipses in the images 206. The shape (e.g. minor to major axis ratio) and relative positioning of the ellipses is dependent on the angle at which the impactor 10 is located. Following from this, feature detection can be used to determine the inclination and anteversion angles for the impactor 10, and these angles can be presented by the processor 203 substantially in 'real time' on the images 206, e.g., within boxes 2011a, 2011b in the image 206 as shown in FIG. 20. This enables a surgeon to move the impactor 10 to the desired orientation based on observation of changes to the displayed angles. Alternatively or additionally, based on the feature detection and user input of the desired inclination and anteversion angles, a second marker can be overlaid on the images to guide movement of the impactor 10 to the desired orientation.

Figure 24:
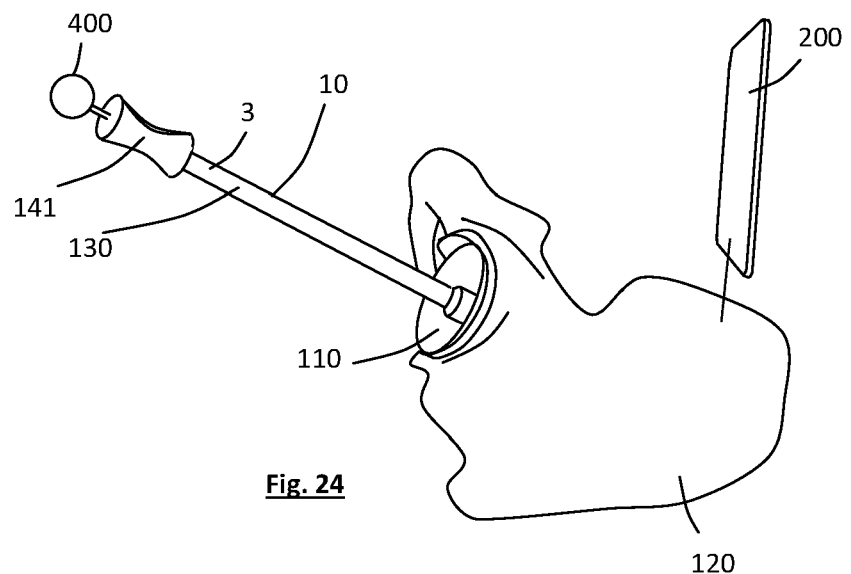
FIG. 24 shows apparatus according to another embodiment of the present disclosure.
Figure 25:
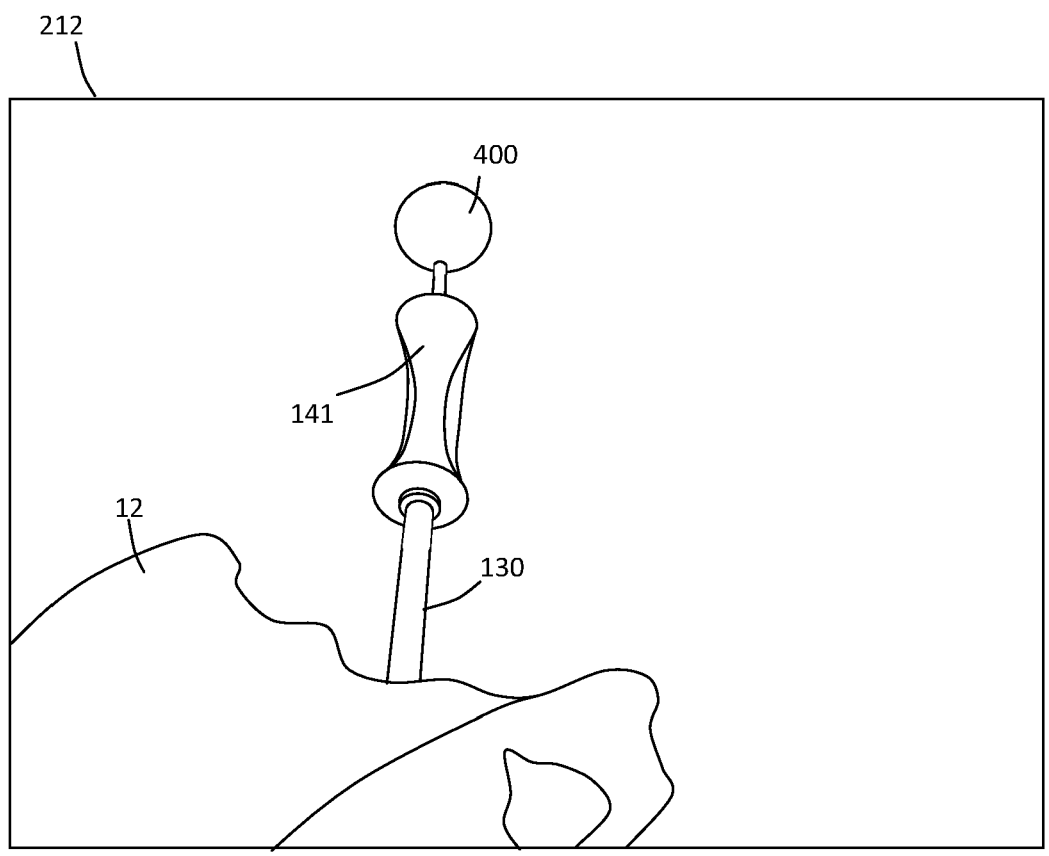
FIG. 25 shows an image of an acetabular cup impactor captured by a camera of the apparatus of FIG. 24.

With reference to FIG. 24, in an alternative embodiment, apparatus is provided that is substantially identical to the apparatus shown in FIG. 19, but which employs a different type of navigation element, in particular a navigation element in the form of a sphere 400 that is releasably mounted at the distal end of the impactor 10. The sphere 400 provides a first marker. With reference to FIG. 25, which shows an example image (frame) 212 as presented on the display, the first marker 400 is visible in the image 212.

Figure 26A:
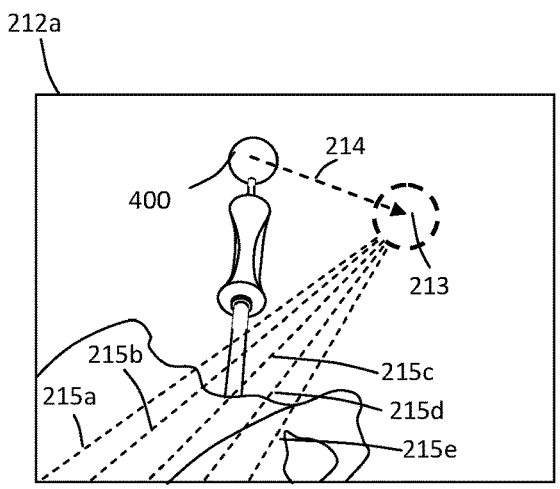
FIGS. 26a to 26d show calibration markers overlaid on images captured by the camera of the apparatus of FIG. 24.
Figure 26B:
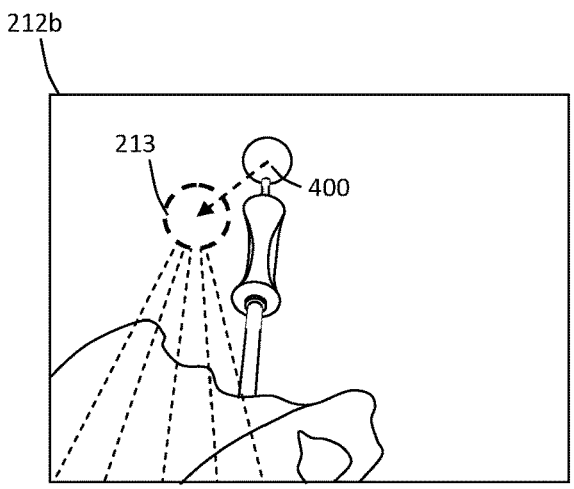
Figure 26C:
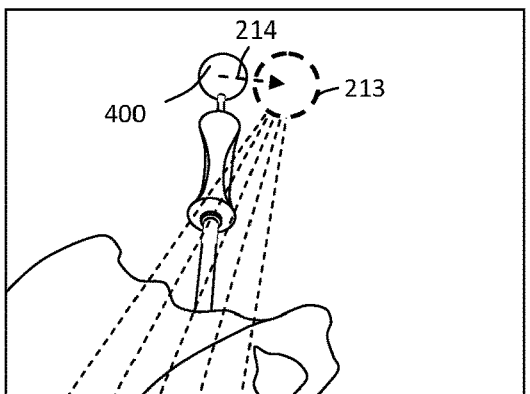
Figure 26D:
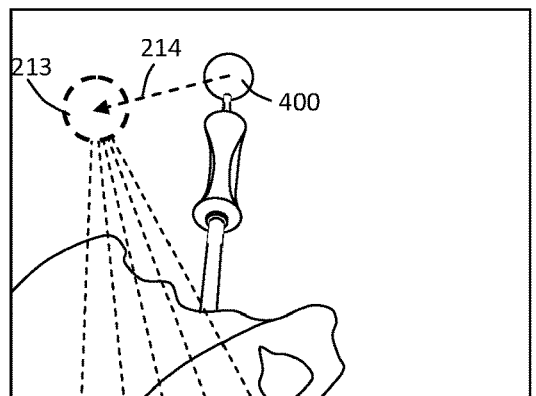
Figure 27:
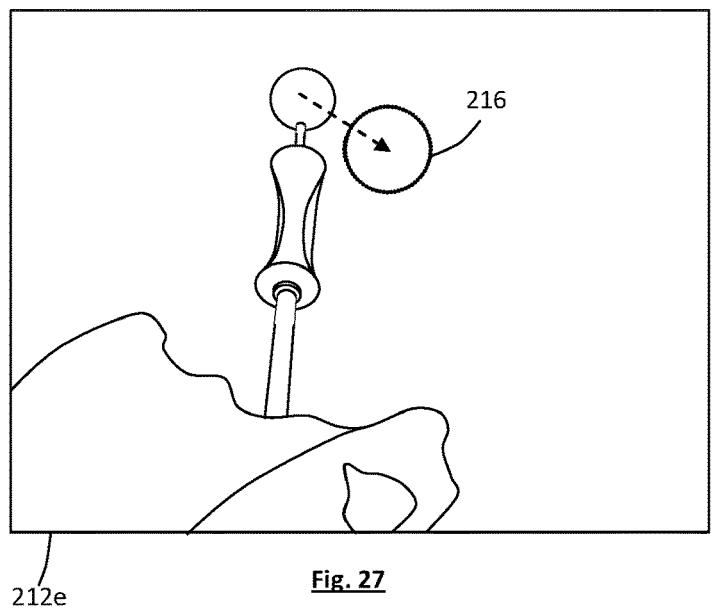
FIG. 27 shows an alignment marker overlaid on an image captured by the camera of the apparatus of FIG. 24.

Again, in this embodiment, a calibration procedure is performed to determine the pivot point of the impactor relative to the camera 201, and the positions of the first marker 400 along the longitudinal axis of the impactor 10. With reference to FIG. 26a, during the calibration procedure the processor 203 is adapted to overlay a third marker 213 in a first position in images 212a displayed by the display device. The impactor 10 is then moved by the surgeon, generally as indicated by arrow 214, such that the first marker 400 is aligned with the third marker 213. Once aligned, the user is required to touch the screen, or 'click', at one of a plurality of guidelines 215a-215e that are overlaid on the screen, which guideline 215a-215e has the closest angular relationship to the angle of extension of the shaft 130 as seen within the image 212a. This process is repeated for a number of different positions (e.g. second to fourth positions) of the third marker 213, as represented in images 212b-212d of FIGS. 26b to 26d. This enables a determination to be made of the positioning of the first marker 400 and the angle of extension of the shaft 130 of the impactor 10 within the images, and through application of trigonometric functions, calibration data including the pivot position of the impactor relative to the camera, and the positions of the first marker along the longitudinal axis of the impactor, can also be determined.

Based on the calibration data and the received orientation data (i.e. the desired inclination and anteversion angles), the processor 203 is adapted to determine where in images a second marker 216 should be located to guide the impactor 10 so that it has the desired inclination and anteversion angles. In this embodiment, with reference to FIG. 24, the processor 203 is adapted to overlay the second marker 216 in the images 212e displayed by the display device 22 such that, when the sphere 400, as seen in the images, is substantially aligned with the second marker 216, the acetabular cup impactor 10 will be oriented at the desired orientation.

While the use of navigation elements, feature detection, and calibration steps, etc., is described in conjunction with FIGS. 19 to 27, where the image capture device is mounted to the pelvic region, substantially the same navigation elements, feature detection, and calibration steps, etc., may be employed, mutatis mutandis, when the image capture device is mounted on the impactor 10, e.g. as shown in FIG. 12. In this variation, navigation elements similar to those described in FIGS. 17 to 24 may be mounted on the pelvic region, for example.

In embodiments described above, calibration of the electronic device 2 is performed by fixing the device 2 relative to the pelvis of a patient with an aim of determining a three dimensional reference frame of the pelvis for hip arthroplasty procedures. Aspects of the present disclosure are not, however, limited to procedures on the hip or limited to arthroplasty procedures. For example, in some embodiments, instead of fixing the device 2 to the pelvis of a patient, the device 2 may be fixed to other bone regions of the patient, such as a vertebra, the skull, the sacrum, a scapula, or a knee (femur or tibia). In some embodiments, the device 2 may not be fixed directly to the patient, but instead may be fixed relative to a patient. For example, the device may be fixed to a surgical table or chair, provided the patient is held steady relative to the surgical table or chair during calibration.

Additionally or alternatively, once the device 2 has been calibrated ('zeroed'), the device 2 may be in some embodiments be transitioned to a device other than the impactor 1. In some embodiments, the device 2 may be used to align a medical tool other than an acetabular cup impactor, such as a surgical drill, a surgical awl or a guide wire. In such circumstances, the device 2 may be coupled to one of these devices in a similar manner to that described above in respect of the impactor 1.

Figure 28A:
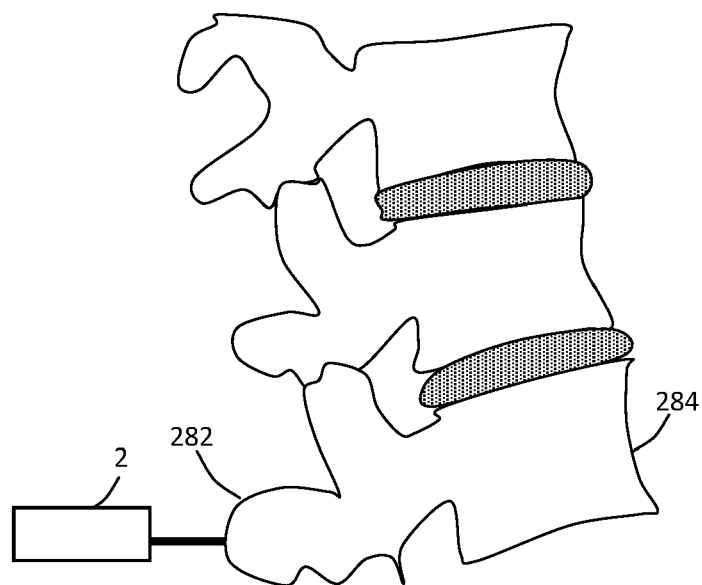
FIGS. 28a and 28b show the electronic device of FIG. 1 coupled to a vertebra.
Figure 28B:
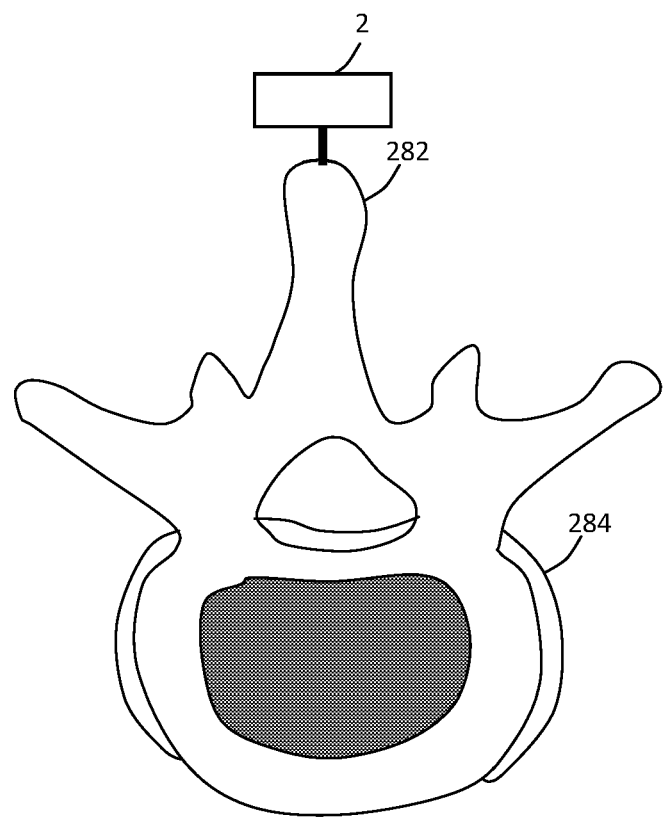

FIGS. 28a and 28b show an embodiment in which the device 2 is utilized for an application other than hip arthroplasty. In particular, FIGS. 28a and 28b show the device 2 coupled to a spinous process 282 of a vertebra 284 of a body. With the device 2 fixed to the vertebra 284, the calibration process described above with reference to FIGS. 4 to 8 may be performed to obtain a reference frame for the device 2 relative to the vertebra 284.

Figure 29:
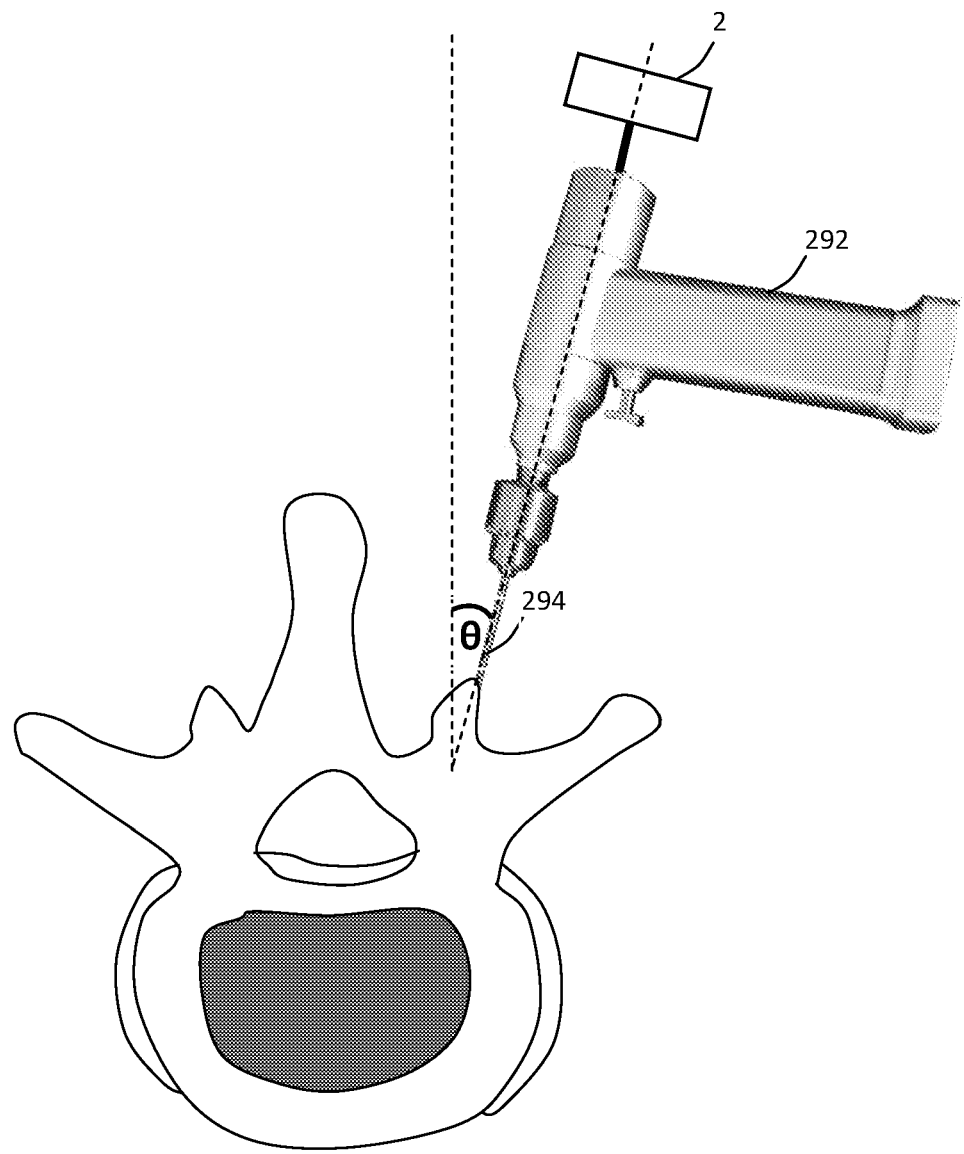
FIG. 29 shows the electronic device of FIG. 1 coupled to a surgical drill used to drill a pilot hole in a vertebra for a medical implant

With the electronic device 2 calibrated relative to the vertebra 284, the device 2 may then be transitioned as shown in FIG. 29 from the fixed location on the spinous process 282 to a fixed location on a surgical drill 292. The angle of inclination and anteversion of the drill relative to the spinous process 282 may then be monitored in a similar manner to that described above for the cup impactor 1 with reference to FIGS. 9 to 14. Using the device 2 coupled to the drill 292, a surgeon can accurately determine the angle of trajectory of the drill bit 294 (or pedicle screw) as he drills into the vertebra.

Embodiments of the present invention have application in anterior cruciate ligament (ACL) reconstruction surgery. During ACL reconstruction surgery, tunnels are drilled in the tibia and femur to which an ACL graft is attached. The ACL graft is provided to replicate the function of the original, damaged ACL. It is important that the position and angle of the tibial and femoral tunnels, to which the ACL graft is attached, is accurately controlled to prevent impingement of the ACL graft on the intercondylar roof and posterior cruciate ligament of the knee. Due to the variation in extension of the knee joint from patient to patient, the required tunnel angle and position also varies.

Figure 30A:
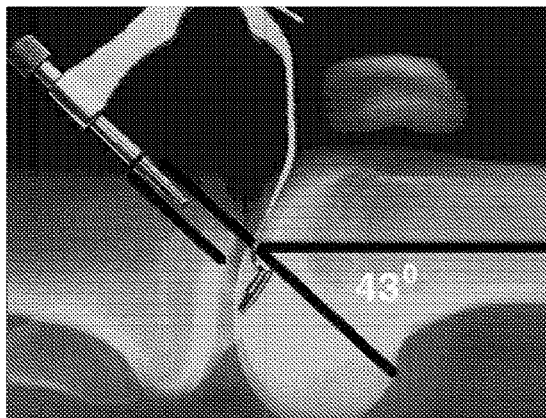
FIGS. 30a and 30b are radiographic images illustrating drilling angles for an anterior cruciate ligament (ACL) reconstruction.
Figure 30B:
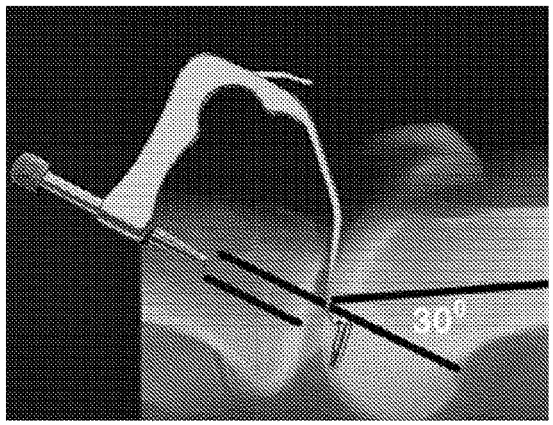

This is illustrated in FIGS. 30a and 30b, which show radiographs of two different knees having different knee extensions and roof angles. The knee shown in the radiograph in FIG. 30a does not hyperextend and has a relatively horizontal intercondylar roof (approx. 43°) as shown by the black lines superimposed over the radiograph. An ACL graft placed in a knee with this anatomical combination would not have roof impingement even though the tibial tunnel appears anterior. In contrast the knee shown in the radiograph in FIG. 30b does hyperextend and has a relatively vertical intercondylar roof (approx. 30°). An ACL graft placed in a knee with this anatomical combination would require a more posterior placement for the tibial tunnel to avoid roof impingement.

Figure 31A:
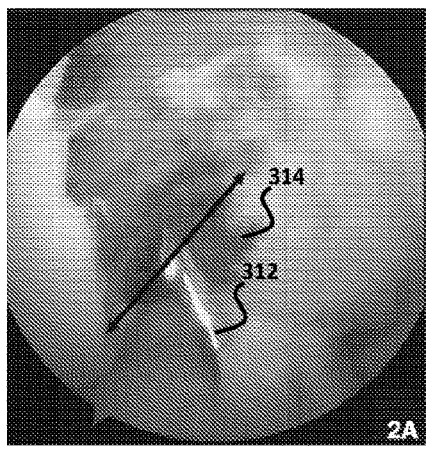
FIG. 31a is an arthroscopic image illustrating drilling angles for an anterior cruciate ligament (ACL) reconstruction.
Figure 31B:
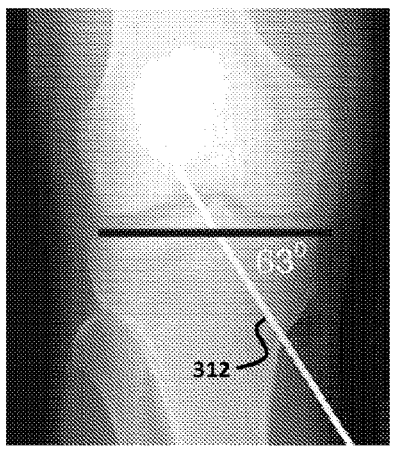
FIGS. 31b and 31c are radiographic images illustrating drilling angles for an anterior cruciate ligament (ACL) reconstruction.
Figure 31C:
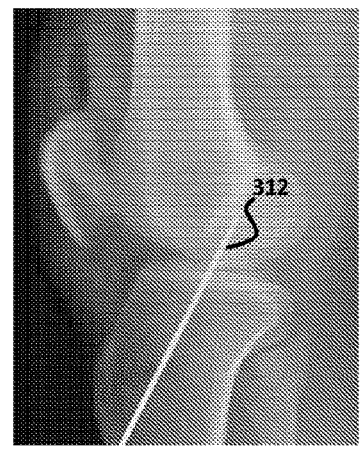

FIGS. 31a, 31b and 31c are arthroscopic and radiographic images of a conventional method for drilling of a tibial tunnel during ACL reconstruction. A tibial tunnel guidewire 312 is guided by a surgeon through an incision in the knee into the tunnel notch 314 (FIG. 31a) with the checkpoint being the centering of the guidewire midway between the apex and base of the lateral half of the notch without crossing the bottom half of the posterior cruciate ligament (PCL). As shown in FIG. 31b, the guidewire 312 should also form an angle of approximately 63° (range, 60° to 65°) with respect to the medial joint line of the tibia. A further checkpoint is shown in FIG. 31c as the alignment of the guidewire 312 4 to 5 mm posterior and parallel to the intercondylar roof with the knee in maximum extension.

Having regard for the above, it will be appreciated that the device 2 may be used to accurately determine the relative angle and displacement of the guidewire 312 relative to parts of the knee, such as the femur or tibia. FIG. 32a is as schematic illustration of the device 2 connected to a femur 322 of a body.

With the device 2 fixed to the femur 322, the calibration process described above with reference to FIGS. 4 to 8 may be performed to obtain a reference frame for the device 2 relative to the femur 322.

Additionally or alternatively, movement of the leg relative to the hip may be used to obtain a reference frame for the device 2 relative to the femur 322. For example, with the device 2 attached to the femur, the vector of gravity g may be measured by the magnetic field sensor 22 when the patient is in a supine (or prone) position on a flat surface as shown in FIG. 7a above, the gravity vector corresponding to the anteroposterior axis of the pelvis. The leg (and therefore femur 322) may then be moved (swung or rotated) about the hip. While the leg is being moved about the hip, the device 2 measures and records its orientation. The collected data can then be used to calculate a centre of rotation/swing of the device 2. Placing the femur 322 back in its original position relative to the patient in the supine position, the longitudinal vector of the femur 322 may be estimated based on a vector between the device 2 and the calculated centre of rotation/swing. With knowledge of the longitudinal vector of the femur and the gravity vector (and therefore the anteroposterior axis of the femur), the transverse vector (across the femur) can be calculated, which vector will necessarily extend perpendicularly to both the longitudinal and anteroposterior axes. Thus, an anatomical reference frame of the patient and specifically of the patient's femur, which reference frame includes the anteroposterior axis, the longitudinal axis of the patient as well as the transverse axis can be determined.

With the electronic device 2 calibrated relative to the femur 322, the device 2 may then be transitioned as shown in FIGS. 32b and 32c from the fixed location on the femur 322 to a fixed location on a surgical drill 324 or other instrument. The angle of the guidewire 312 relative to the femur 322 may then be monitored in a similar manner to that described above for the cup impactor 1 and the spinous process 282 with reference to FIGS. 9 to 14 and 28a to 29. Using the device 2 coupled to the drill 324, a surgeon can accurately determine the angle of trajectory of the guidewire 312 as he drills the femoral tunnel in the femur 322.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An apparatus comprising:
  a medical tool moveable to a desired orientation relative to a bone region of a patient for implantation of a medical implant; and
  an electronic orientation sensor that moves between a first location fixed relative to the bone region of the patient and a second location on the medical tool;
  the electronic orientation sensor records a reference orientation of the bone region of the patient when the orientation sensor is in the first location and,
    measures a gravity vector relative to the orientation sensor;
    determines a longitudinal vector defined by the patient responsive to rotating the bone region about the longitudinal vector to change orientation of the patient relative to the gravity vector; and
    determine a transverse vector defined by the patient based on the gravity vector and the longitudinal vector, and
  the electronic orientation sensor determines an orientation of the medical tool relative to the reference orientation when the orientation sensor is in the second location.

2. The apparatus of 1, wherein the gravity vector is measured relative to the orientation sensor with the patient in a supine position or a prone position, and wherein recording the reference orientation further comprises measuring the gravity vector relative to the orientation sensor with the patient in a lateral position.

3. The apparatus of claim 1, wherein the orientation sensor comprises one or more gravitational field sensors and/or one or more accelerometers and/or one or more magnetic field sensors and/or one or more gyroscopes.

4. The apparatus of claim 1, comprising an output device adapted to provide information about the determined relative orientation of the medical tool and/or the recorded reference orientation to a clinician or other user.

5. The apparatus of claim 1, wherein the medical tool comprises an acetabular cup impactor configured to allow implanting an acetabular cup in an acetabulum of a pelvic region of the patient.

6. The apparatus of claim 5, wherein the orientation sensor is measures a pelvic tilt range of the patient based on a difference between a measured maximum posterior tilt of the patient and a measured maximum anterior pelvic tilt of the patient.

7. The apparatus of claim 6, further comprising processing means configured to determine angles of anteversion and inclination of the acetabular cup relative to the pelvic region in dependence on the measured pelvic tilt range.

8. The apparatus of claim 1, wherein the medical tool comprises a guide wire or a surgical drill configured to allow implanting an ACL graft to the patient.

9. A method of positioning an acetabular cup impactor, comprising:
  locating an electronic orientation sensor at a first location fixed relative to a bone region of a patient,
  using the electronic orientation sensor located at the first location to record a reference orientation of the patient's bone region by:
    measuring a gravity vector relative to the orientation sensor;
    determining a longitudinal vector of the patient based on a change of orientation of the patient relative to the gravity vector; and
    determining a transverse vector of the patient based on the determined gravity vector and the determined longitudinal vector, wherein the change orientation comprises a rotation of the bone region about the longitudinal vector;
  transitioning the electronic orientation sensor from the first location to a second location on a medical tool, the medical tool being moveable to a desired orientation relative to the patient's bone region for implantation of a medical implant, and using the orientation sensor located at the second location to determine an orientation of the medical tool relative to the reference orientation.

10. The method of claim 9, wherein the gravity vector is measured with the patient in a lateral position, and wherein recording the reference orientation further comprises measuring the gravity vector relative to the orientation sensor with the patient in a supine position.

11. A non-volatile machine-readable medium comprising instructions stored therein, which when executed by a processor, causes the processor to perform the method of claim 9.

* * * * *